(12) United States Patent
Ozawa

(10) Patent No.: US 7,176,301 B2
(45) Date of Patent: Feb. 13, 2007

(54) NITRATE INDUCIBLE PROMOTER

(75) Inventor: Hidenori Ozawa, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 70 days.

(21) Appl. No.: 11/094,278

(22) Filed: Mar. 31, 2005

(65) Prior Publication Data

US 2006/0225145 A1    Oct. 5, 2006

(51) Int. Cl.
*C12N 15/63*    (2006.01)
*C12N 15/82*    (2006.01)
*C12N 5/04*    (2006.01)
*C12N 15/29*    (2006.01)

(52) U.S. Cl. .................. 536/24.1; 435/320.1; 435/468; 435/419; 800/278

(58) Field of Classification Search .................... None
See application file for complete search history.

*Primary Examiner*—David T. Fox
*Assistant Examiner*—Brent T Page
(74) *Attorney, Agent, or Firm*—Birch, Stewart, Kolasch & Birch, LLP

(57) ABSTRACT

A promoter comprising any one selected from the group consisting of the nucleotide sequence of SEQ ID No: 7, the nucleotide sequence of SEQ ID No: 8, the nucleotide sequence of SEQ ID No: 9, the nucleotide sequence of SEQ ID No: 10, the nucleotide sequence of SEQ ID No: 11 and the nucleotide sequence of SEQ ID No: 12, which is capable of inducing the expression of a downstream gene of the promoter under the presence of nitrate.

6 Claims, 2 Drawing Sheets

NITRATE INDUCIBLE PROMOTER

BACKGROUND OF THE INVENTION

1. Field of the Invention

The present invention relates to a promoter. More specifically, the present invention relates to a promoter capable of regulating, by means of external stimulus, the gene expression of a foreign protein that is inserted into the downstream of the promoter.

2. Description of the Related Art

It is known that nitrogen is an important nutrient for plants and thus most of plants have a nitrate-phile property, and that the proliferation of plant culture cells and the growth of a plant are greatly affected by the presence or absence of a nitrate or its concentration. A group of proteins functioning when a plant absorbs nitrate from its roots and transports the absorbed nitrate from a cell to another cell in the plant are known as nitrate transporter proteins.

Nitrate transporter proteins are known to include low-affinity nitrate transporters which function at the time when the nitrate concentration is high (i.e., 0.5 mM or more) and high-affinity nitrate transporters which function at the time when the nitrate concentration is low (i.e., 0.5 mM or less). A gene encoding each of two types of the nitrate transporters (hereinafter, also referred to as a low-affinity nitrate transporter gene and a high-affinity nitrate transporter gene) is reported (Kagaku to Seibutsu (Chemistry and Biology), Vol. 38, pp. 196–203, 2000). As a result of the progress of the study on molecular biology so far, the low-affinity nitrate transporter genes are reported to include CHL1 (AtNRT1) derived from *Arabidopsis thaliana* (Cell, Vol. 72, pp. 705–713, 1993; The Plant Cell, Vol. 8, pp. 2183–2191, 1996); NTL1 (AtNRT1:2) derived from *Arabidopsis thaliana* (The Plant Cell, Vol. 11, pp. 1381–1392, 1999); OsNRT1 derived from rice (Plant Physiol., Vol. 122, pp. 379–388, 2000); BnNRT1:2 derived from rapeseed (J. Biol. Chem., Vol. 273, pp. 1201, 1998); and LeNRT1 derived from tomato (Proc. Natl. Acad. Sci. USA, Vol. 93, pp. 8139–8144, 1996). In addition, the CHL1 is also reported to have both functions of low and high affinities (The Plant Cell, Vol. 11, pp. 865–874, 1999). Of these genes, it is experimentally confirmed that CHL1, NTL1 and OsNRT1 have the nitrate transport activity. Besides these genes, although many homologous genes are isolated, they are not determined for nitrate transport activity, and thus they are not shown to be nitrate transporter genes in the present circumstances.

As described above, nitrate transporters have also thus far been investigated for the respective gene and the protein functions and many reports have been published; however, no promoters of nitrate transporter genes have been reported.

In general, a promoter, an expression regulatory region of the gene, is capable of regulating the expression of a gene located downstream of the promoter, and therefore the selection of a promoter to be used for regulating the expression of a foreign gene is important. In other words, the selection of the promoter is important in the preparation of a transgenic plant, because the promoter is capable of controlling the stage, tissue and intensity in the expression of the foreign gene. Methods that are frequently used to express a foreign gene in a plant cell include a method of connecting a foreign gene to the downstream of a CaMV 35S promoter, or a nopaline synthase gene promoter (Sander P. R. et al., Nucleic Acid RES, 15 (1987) 1543–1558), etc. Methods of regulating, by the application of external stimulus, the expression of a foreign gene have been reported; examples include a method of making use of a promoter of the α-amylase gene (Chan M. T. et al., J. Biol. Chem., 269 (1994) 17635–17641), a promoter of the phosphate transporter gene (N. Mitsukawa et al., Proc. Natl. Acad. Sci. USA, 94 (1997) 7098–7102), or a damage-inducible promoter (T. Yamada et al., Plant cell Physiol. (1994) 917–926), a chemical-inducible promoter (Ward et al., Plant Mol. Biol., 22 (1993) 361–366), and a photoinducible promoter (Fluhr et al., Science, 232 (1986) 1106–1112). However, the presence of a promoter that induces the expression of a gene by means of nitrate stimulus has never been reported.

BRIEF SUMMARY OF THE INVENTION

It is an object of the present invention to provide of a nitrate inducible promoter capable of regulating the expression of a downstream gene by means of the presence of nitrate.

The present invention provides a promoter selected from the group consisting of the following (a) to (f):

(a) a promoter comprising the nucleotide sequence of SEQ ID No: 7 that is capable of inducing the expression of a downstream gene of the promoter under the presence of nitrate;

(b) a promoter comprising the nucleotide sequence of SEQ ID No: 8 that is capable of inducing the expression of a downstream gene of the promoter under the presence of nitrate;

(c) a promoter comprising the nucleotide sequence of SEQ ID No: 9 that is capable of inducing the expression of a downstream gene of the promoter under the presence of nitrate;

(d) a promoter comprising the nucleotide sequence of SEQ ID No: 10 that is capable of inducing the expression of a downstream gene of the promoter under the presence of nitrate;

(e) a promoter comprising the nucleotide sequence of SEQ ID No: 11 that is capable of inducing the expression of a downstream gene of the promoter under the presence of nitrate; and (f) a promoter comprising the nucleotide sequence of SEQ ID No: 12 that is capable of inducing the expression of a downstream gene of the promoter under the presence of nitrate.

Further, the present invention provides the following means:

(1) An expression vector containing a promoter of the present invention.

(2) A cell having expression vector containing a promoter of the present invention.

(3) A transformant comprising a cell having an expression vector containing a promoter of the present invention.

(4) A method of regulating the amount of expression of a downstream gene of a promoter of the present invention in a cell having an expression vector containing the promoter, comprising regulating the concentration of nitrate in the environment where the cell is placed.

(5) A method of regulating the amount of expression of a downstream gene of the promoter of the present invention in a transformant comprising a cell having an expression vector containing the promoter, comprising regulating the concentration of nitrate in the environment where the cell is placed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

Figure 1:
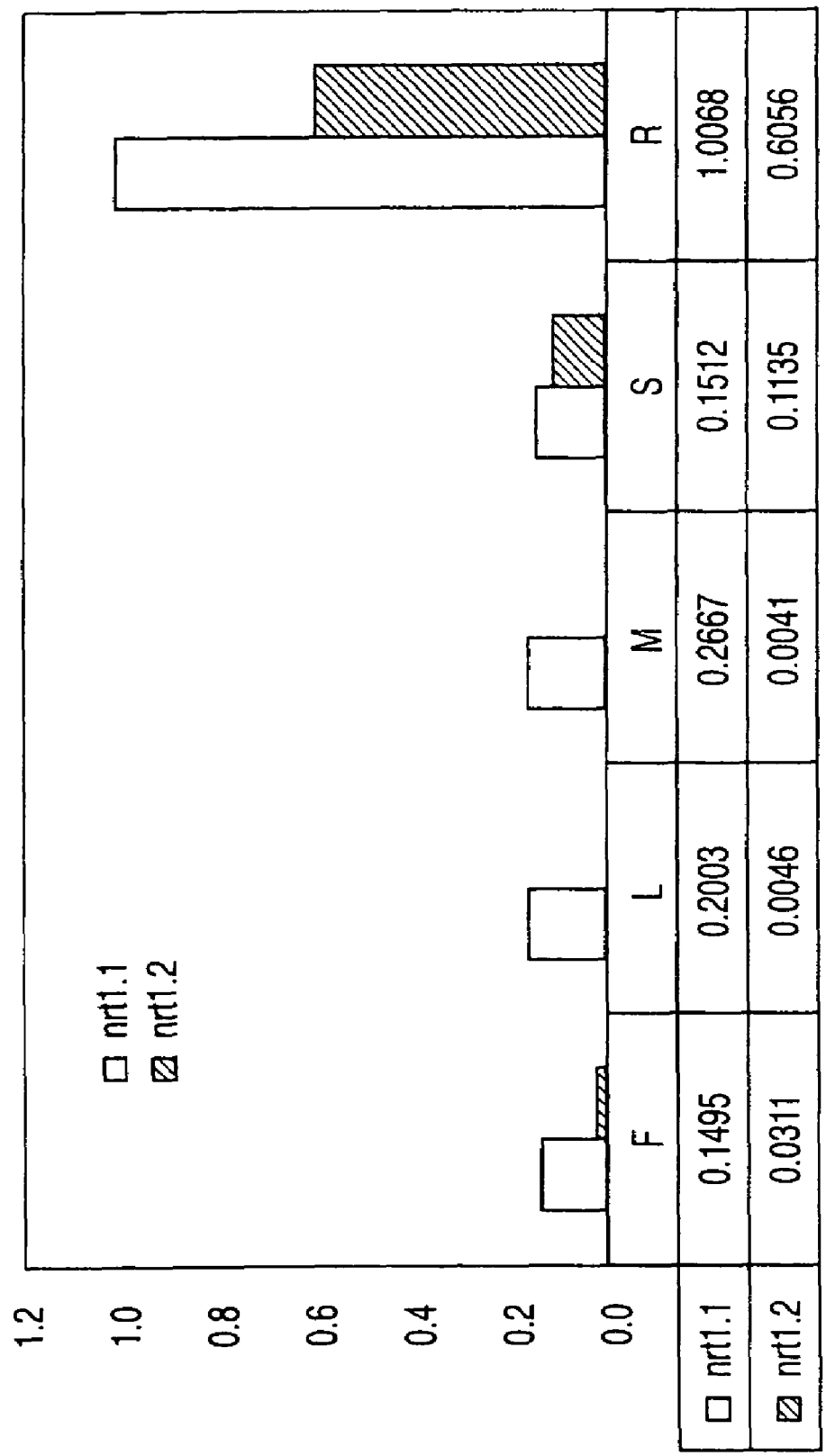
FIG. 1 is a diagram indicating the amounts of expression of Group nrt1.1 and Group nrt1.2 in each organ of a tobacco plant.

The present invention will be set forth in detail hereinafter; however, the descriptions below are simply for explaining the invention, and the invention is by no means limited thereto. Additionally, in the descriptions below, general techniques used in genetic recombination, such as the cutting and ligation of DNA, the transformation of *E. coli*, the nucleotide sequence determination of a gene, and PCR, can be carried out with reference to instructions attached to commercially available reagents or machinery to be used in each operation and experimental manuals (e.g., Molecular cloning, Maniatis T. et al. Cold Spring Harbor Laboratory Press).

1. Nitrate Inducible Promoter of the Present Invention
(1) Isolation Method of the Promoter A promoter of the present invention can induce the expression of a downstream gene of the promoter under the presence of nitrate. As such, a promoter of the present invention is also called a nitrate inducible promoter.

The present inventors tried to isolate the upstream region of a gene encoding a protein closely related to nitrate uptake, for the purpose of isolating such a nitrate inducible promoter. First of all, a plurality of types of nitrate transporter genes were isolated that encode proteins closely related to nitrate uptake (refer to Example 1 as will be described later below). Isolated four types of nitrate transporter genes are referred to nrt1.1A, nrt1.1B, nrt1.2A and nrt1.2B, and nucleotide sequences of these genes are respectively represented by SEQ ID No: 13, 15, 17, and 19. Next, the upstream regions of the respective isolated nitrate transporter genes were isolated (refer to Example 2 as will be described later below).

A method of isolating the upstream region of nitrate transporter genes will be described below. A pair of oligonucleotide primers (SEQ ID No: 25 and 26) is prepared based on the consensus nucleotide sequence of the isolated nitrate transporter genes (SEQ ID No: 13, 15, 17 and 19). By means of the inverse-PCR method using a pair of oligonucleotides (SEQ ID No: 25 and 26) as primers, the upstream regions of the nitrate transporter genes can be isolated from chromosomal DNA of a plant. More specifically, in the inverse-PCR method, a DNA sample which has been prepared by having completely digested chromosomal DNA of a plant with a restriction enzyme and self-ligating is used as a template, and a pair of oligonucleotides which has been prepared from consensus sequence of the nitrate transporter genes are used as primers. The inverse-PCR enables the isolation of the upstream regions of the nitrate transporter genes. The isolated upstream regions are subjected to nucleotide sequence analysis, and as a result, the sequences of the upstream regions of the nitrate transporter genes can be determined.

(2) Features of the Promoters

As described above, the upstream regions of the nitrate transporter genes were isolated utilizing the consensus sequence of the obtained plurality of nitrate transporter genes, and the sequences of the upstream regions were determined. The determined sequences of the upstream regions are shown in SEQ ID No: 1 to 6. The sequences corresponding to the upstream regions of the nitrate transporter genes nrt1.1A and nrt1.1B are represented by SEQ ID No: 1 and 2, respectively. The sequences corresponding to the upstream regions of the nitrate transporter gene nrt1.2A or nrt1.2B are represented by SEQ ID No: 3 to 6. Basically, for the upstream regions of nrt1.2A and nrt1.2B, only one sequence for each region should be isolated, but four nucleotide sequences of the upstream regions (SEQ ID No: 3 to 6) were obtained in the example as described later. This would seem to be because other nitrate transporter genes were present in addition to nrt1.1A, nrt1.1B, nrt1.2A and nrt1.2B in the plant and the upstream regions thereof were also isolated. Any one of the sequences of SEQ ID No: 3 to 6 obtained in the after-mentioned example corresponds to either of the upstream regions of nrt1.2A or nrt1.2B. However, whether the sequences of SEQ ID No: 3 to 6 correspond to the sequence of the upstream region of nrt1.2A or nrt1.2B is not determined by means of the example as described later.

In the present invention, by the investigation of the expression of the nitrate transporter gene Group nrt1.1 (nrt1.1A and nrt1.1B) and Group nrt1.2 (nrt1.2A and nrt1.2B), the sensitivity of the promoter regions of these genes to nitrate was studied. On the basis of this study, promoters of the present invention were characterized (see Examples 3 and 4 as described later below). More specifically, the investigations were carried out as to a tissue where the nitrate transporter gene Groups nrt1.1 and nrt1.2 express (Example 3), and as to how the expression changes in response to the nitrate concentration (Example 4).

Figure 2A:
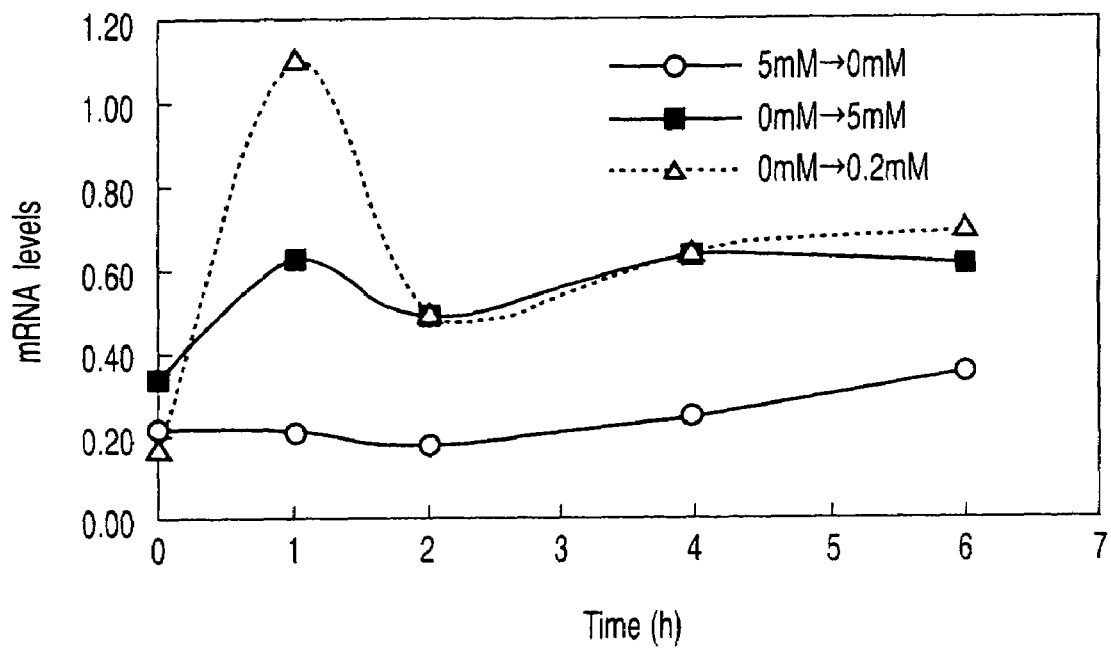
FIG. 2A is a diagram indicating the effects of nitrate on the expression of Group nrt1.1.
Figure 2B:
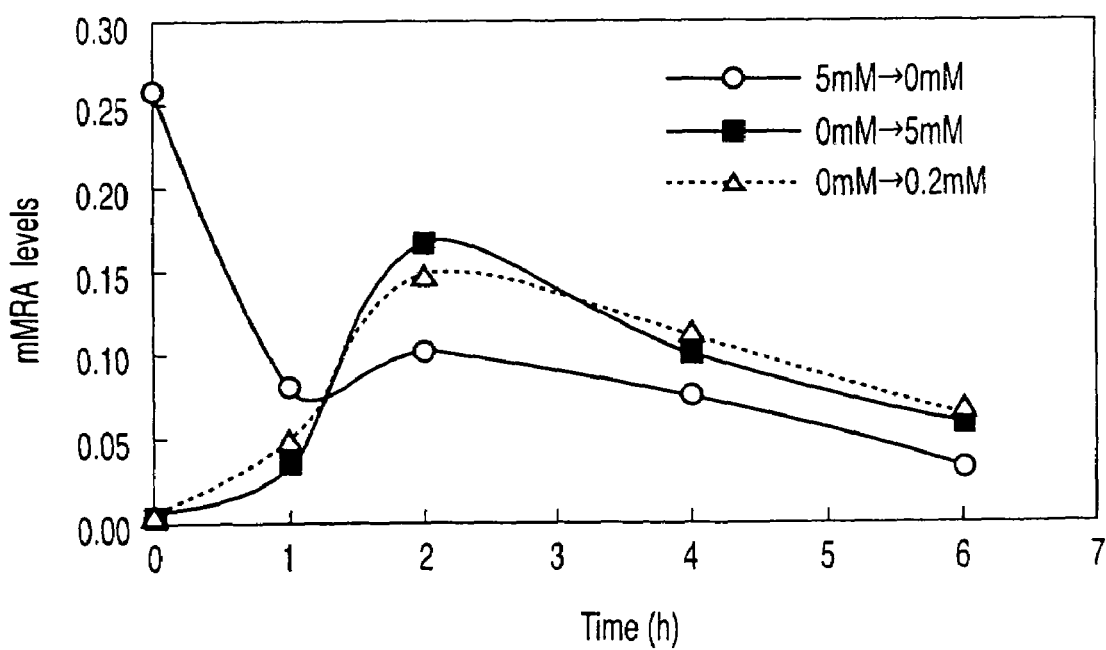
FIG. 2B is a diagram indicating the effects of nitrate on the expression of Group nrt1.2.

Group nrt1.1 was expressed in all the organs of a tobacco plant; Group nrt1.2 was expressed in specific tissues (primarily in roots, secondarily in stems and flowers) (FIG. 1). The expression of Group nrt1.1 was constitutively maintained not depending on the presence or absence of nitrate and the addition of nitrate increased its expression (FIG. 2A). On the other hand, Group nrt1.2 was rarely expressed in the absence of nitrate and the addition of nitrate induced its expression (FIG. 2B).

Accordingly, the promoter located in the upstream of Group nrt1.1 enables the constitutive expression of a downstream gene in all the organs of a plant, and the promoter has a property of increasing the expression in the presence of nitrate. On the other hand, the promoter located in the upstream of Group nrt1.2 has a property of inducing the expression of downstream gene in specific tissues, particularly in roots, only after the presence of nitrate.

Further, a reporter gene is connected to the downstream of the nucleotide sequences of the upstream regions described in SEQ ID No: 1 to 6 and then the expression of the reporter gene is verified. As a result, it is proved that the nucleotide sequences of the upstream region described in SEQ ID No: 1 to 6 can function as nitrate inducible promoters (refer to Examples 5 and 6 as described later below).

These nucleotide sequences of the upstream regions indicated by SEQ ID No: 1 to 6 include the TATA box, which is a DNA element required for transcription initiation reaction. Specifically, the 617 to 623 positions of the nucleotide sequence indicated by SEQ, ID No: 1, the 821 to 827 positions of the nucleotide sequence indicated by SEQ ID No: 2, the 941 to 947 positions of the nucleotide sequence indicated by SEQ ID No: 3, the 704 to 710 positions of the nucleotide sequence indicated by SEQ ID No: 4, the 810 to 816 positions of the nucleotide sequence indicated by SEQ ID No: 5, and the 1009 to 1015 positions of the nucleotide sequence indicated by SEQ ID No: 6 correspond to the TATA box. It is confirmed that these TATA boxes are sequences necessary for promoter activity by the investigation on the promoter activities of deletion promoters in which the sequences of the upstream regions of the nitrate transporter genes were cut into various lengths (see Example 6 as described later below).

Hence, a nitrate inducible promoter of the present invention may be defined as a promoter that includes at least the sequence from the TATA box to the initiation codon of the nitrate transporter gene (wherein the TATA box itself is included, but the initiation codon itself is excluded) and exhibits promoter activity. With respect to the sequences of the upstream regions as indicated in SEQ ID No: 1 to 6, the sequences from the TATA boxes to the initiation codons of the nitrate transporter genes (wherein the TATA boxes are included, but the initiation codons are excluded) are respectively expressed in SEQ ID No: 7 to 12. The nitrate inducible promoters of the present invention may have arbitrary length as long as the promoters include any one of the nucleotide sequences of SEQ ID No: 7 to 12 and the promoter can induce the expression of a downstream gene of the promoter under the presence of nitrate. Additionally, a nitrate inducible promoter of the present invention may be subjected to one or a few bases of substitution, deletion, or addition in its nucleotide sequence, or one or a few bases of chemical modification in its nucleotide sequence as long as the promoter activity can be maintained. Such partially modified promoters are also included within the scope of the present invention.

In the present invention, the phrase "the expression of a downstream gene of the promoter is induced under the presence of nitrate" includes the following cases. The meaning of the phrase includes the case where the downstream gene that was not expressed under the absence of nitrate is expressed only after the presence of nitrate and the case where the amount of expression of the downstream gene that was expressed under the absence of nitrate is increased after the presence of nitrate. In these cases, the presence of nitrate means, for example, a nitrate concentration of 0.1 to 10 mM, preferably a nitrate concentration of 0.2 to 5 mM. However, the nitrate concentration necessary to induce the expression of a downstream gene is not limited to the above range of nitrate concentration, and is preferably set based on the study on the sensitivity of each promoter to nitrate.

Nitrate inducible promoters of the present invention include promoters having promoter activity among the deletion promoters prepared in Example 6 as described later below.

In the sequences of SEQ ID No: 1 to 6 (the sequences of the upstream regions of the nitrate transporter genes) and the sequences of SEQ ID No: 7 to 12 (the sequences essential for the promoter), the untranslated region (UTR) of the 5' side is indicated by "5'UTR" in the column of <220> of the Sequence Listing below.

2. Expression Vector Containing Promoters of the Present Invention

Further, the present invention can provide an expression vector containing the above "nitrate inducible promoter of the present invention", a gene encoding a target protein located downstream of the promoter, and a terminator for terminating the transcription of the gene, in accordance with a method well known in the art. Such an expression vector is capable of inducing the expression of a gene encoding a target protein under the presence of nitrate. In the present invention, a gene encoding a target protein may be a nitrate transporter gene, or other arbitrary genes whose expression is intended to be regulated depending on the presence of nitrate.

An expression vector of the present invention may further contain a marker gene (e.g., a drug resistance gene) for selecting a transformant having the expression vector. Also, when an expression vector of the present invention is used in the known *Agrobacterium* infection method, the vector is preferably prepared on the basis of the binary vector derived from the Ti plasmid of *Agrobacterium*.

3. Cell having an Expression Vector Containing a Promoter of the Present Invention Still further, the present invention can provide a transformed cell that is prepared by introducing the above "an expression vector containing a promoter of the present invention" into an arbitrary cell in accordance with a method well known in the art. For instance, an expression vector containing the above promoter of the present invention can be introduced into *Agrobacterium*. The resultant transformed *Agrobacterium* enables a target protein-encoding gene in the expression vector contained in the *Agrobacterium* to be introduced into a plant by infectivity of the *Agrobacterium* in the plant.

4. Transformant Comprising a Cell Having an Expression Vector Containing a Promoter of the Present Invention Furthermore, the present invention can provide a transformant comprising the above "cell having an expression vector containing a promoter of the present invention" in accordance with a method well known in the art. For example, *Agrobacterium* having an expression vector containing a promoter of the present invention can be introduced into a plant or a plant cell through the use of infectivity of the *Agrobacterium* in the plant.

In general, as the transformation method of plants or plant cells are known a variety of methods. The examples include particle gun method, PEG method, electroporation method, and *Agrobacterium* infection methods such as leaf disk method and vacuum infiltration method. When a plant cell is transformed by the particle gun method, the PEG method, or the electroporation method, a vector replicable in *E. coli* such as commercially available pUC19, or pBluescript can be used as a transformation vector. When a plant or a plant cell is transformed by the *Agrobacterium* infection methods such as leaf disk method or vacuum infiltration method, a vector derived from Ti plasmid such as pGV3850 (De Block M et al., EMBO J., 3 (1984) 1681–1689) or a binary vector such as pBI121 (Clonetech) can be used as a transformation vector.

5. Method of Regulating the Amount of Expression of a Downstream Gene of a Promoter of the Present Invention Further, the present invention provides a method of regulating the amount of expression of a downstream gene of a promoter of the present invention in a cell having an expression vector containing the promoter. Also, the present invention provides a method of regulating the amount of expression of a downstream gene of a promoter of the present invention in a transformant comprising a cell having an expression vector containing the promoter.

In the method of the present invention, the expression of a downstream gene of a promoter of the present invention can be regulated in accordance with nitrate sensitivity of the promoter. More specifically, when a promoter derived from an upstream region of Group nrt1.1 (i.e., a promoter containing at least the nucleotide sequence described in SEQ ID No: 7 or 8) is used, the invention enables the expression of a foreign gene regardless of the presence or absence of nitrate in all the organs of a plant, as well as enabling an increase in the amount of the expression by the addition of nitrate (see FIG. 2A). On the other hand, when a promoter derived from an upstream region of Group nrt1.2 (i.e., a promoter containing at least of the nucleotide sequences described in any one of SEQ ID No: 9 to 12) is used, the invention can induce the expression of a foreign gene only under the presence of nitrate in a specific organ alone (see FIG. 2B).

EXAMPLES

The present invention will be specifically set forth by Examples hereinafter; however, the invention is by no means limited to the descriptions below.

Example 1

Isolation of Low-Affinity Nitrate Transporter Gene (1) Extraction of the Total RNA of *Nicotiana tabacum* cv. Burley 21

*Nicotiana tabacum* cv. Burley 21 are cultivated for 2 to 3 weeks in a standard hydroponic solution (5 mM $KNO_3$, 2.5 mM potassium phosphate buffer (pH 5.5), 2 mM $MgSO_4$, 2 mM $Ca(NO_3)_2$, 0.05 mM Fe-EDTA, 70 µM $H_3BO_3$, 14 µM $MnCl_2$, 0.5 µM $CuSO_4$, 1 µM $ZnSO_4$, 0.2 µM $NaMoO_4$, 10 µM NaCl, and 0.01 µM $CoCl_2$), and then the obtained roots were used for the preparation of the total RNA. 0.5 g of the root was placed into a tube of Fast RNA-Green Kit (BIO 101) and the tube was placed in a FastPrep FP120 apparatus to homogenize the root. The total RNA was prepared in accordance with the protocol attached.

(2) Isolation of Low-Affinity Nitrate Transporter Genes by the RT-PCR Method

The reverse transcription reaction was carried out using the obtained total RNA as a template. More specifically, the reaction mixture containing 1 to 2 µg of the total RNA, 10×RT buffer, a final concentration of 0.5 mM of dNTPs, 10 pmol of oligo dT (15) primer, 10 units of an RNase inhibitor (Applied Biosystems), and 1 unit of Omniscript Reverse Transcriptase (Qiagen) was prepared in the total amount of 10 µL using RNase-free water. The resulting reaction mixture was subjected to reverse transcription reaction at 37° C. for 60 minutes, and then was treated at 93° C. for 5 minutes to inactivate the enzyme.

Next, PCR was performed using a portion of the reaction mixture as a template. More specifically, 5 µL of the reaction mixture, 10 µL of 10× buffer, a final concentration of 0.2 mM of dNTP, 10 pmol of primer set, and 5 units of Ex-Taq DNA polymerase (manufactured by TaKaRa) were adjusted to total 50 µL. In PCR, one cycle of 94° C. for 2 minutes was performed; 30 cycles of 94° C. for 30 seconds, 55° C. for 30 seconds and 72° C. for 1.5 minutes was performed; and then one cycle of 72° C. for 7 minutes was performed, using a thermal cycler (GeneAmp PCR System 9700). As the primer set, two types were used: a set of N-1 (5'-ATGGCACTTC CTGAAACACA ACAA-3') and N-2 (5'-TTAGTGGCAA GCTGGTTCTG AATC-3') as shown in SEQ ID No: 21 and 22, and a set of N-3 (5'-ATGGCACTTC CTGAGACACA GC-3') and N-4 (5'-TCAATGACA AACCGGTCCA TCAT-3') as shown in SEQ ID No: 23 and 24.

The two types of primer sets: a set of N-1 and N-2 and a set of N-3 and N-4, were used to yield each about 1.8 kb of amplified PCR products. The respective amplified products were purified by agarose gel electrophoresis and cloned into pUC19 (TaKaRa). The plasmid DNA was extracted from several *E. coli* colonies, labeled with BigDye Terminator Cycle Sequencing Ready Reaction Kit v 2.0 (Applied Biosystems), and then subjected to analysis of the nucleotide sequences by means of ABI PRISM 3700. As a result, it was found that two kinds of amplified PCR products in each primer set were obtained. The nucleotide sequences of the total four PCR products are indicated by SEQ ID No: 13, 15, 17 and 19. The genes consisting of these nucleotide sequences are respectively named to nrt1.1A, nrt1.1B, nrt1.2A and nrt1.2B. The amino acid sequences encoded in these nucleotide sequences are respectively represented by SEQ ID No: 14, 16, 18 and 20.

In this manner, the four low-affinity nitrate transporter genes were isolated by RT-PCR method from the total RNA derived from each organ (e.g., lamina, midrib, stem and root, etc.) of *Nicotiana tabacum* cv. Burley 21.

Example 2

Isolation of the Upstream Region of Low-Affinity Nitrate Transporter Genes

Group nrt1.1 (nrt1.1A and nrt1.1B) and Group nrt1.2 (nrt1.2A and nrt1.2B) had a high degree of homology and thus common sequence portions. Oligonucleotide primers were synthesized on the basis of their common sequence portions. Their nucleotide sequences are: 433–458F: 5'-AAACAACTTATGGTCCTATACATTGC-3' (5' side primer) (SEQ ID No: 25), and 777–751R: 5'-AACTGAAG-CAATTTGTGTCAATGGACT-3' (3' side primer) (SEQ ID No: 26). By use of the primers, clones containing low-affinity nitrate transporter genes were screened by PCR from a Tobacco BAC Library.

A method of preparing the Tobacco BAC Library is as follows. A tobacco chromosomal DNA was digested into fragments by means of HindIII and inserted into a pBA-CLacSp vector. This vector was introduced into an *E. coli* DH10B strain by electroporation to obtain about 100,000 BAC clones having an average length of the inserted fragments of 140 kb.

As described above, PCR was performed using this tobacco BAC Library as a template. As a result, 14 positive clones were obtained. These *E. coli* were cultured in a liquid medium and then the plasmids were extracted. The extracted plasmids were labeled with a BigDye Terminator Cycle Sequencing Ready Reaction Kit ver. 2 (Applied Biosystems), and then subjected to analysis of the nucleotide sequences by means of ABI PRISM 3700. With respect to a primer for the sequencing, an antisense orientation chain of a low-affinity nitrate transporter gene was designed and synthesized.

As a result, nucleotide sequences of the upstream regions of the low-affinity nitrate transporter genes were determined. In the present invention, six types of nucleotide sequences of the upstream regions of the low-affinity nitrate transporter genes were obtained. These six types of nucleotide sequences of the upstream region are indicated by SEQ ID No: 1 to 6. As the sequence corresponding to the upstream region of nrt1.1A, was obtained the nucleotide sequence denoted by SEQ ID No: 1, and as the sequence corresponding to the upstream region of nrt1.1B, was obtained the nucleotide sequence shown in SEQ ID No: 2. As nucleotide sequences corresponding to either of the upstream region of nrt1.2A or nrt1.2B, were obtained the nucleotide sequences indicated by SEQ ID No: 3 to 6. As described in the section of the DETAILED DESCRIPTION, basically, one nucleotide sequence should be isolated from each of the upstream regions of nrt1.2A and nrt1.2B. In this Example, however, the four types of nucleotide sequences of the upstream regions are obtained. This would seem to be because nitrate transporter genes also exist in addition to nrt1.1A, nrt1.1B, nrt1.2A and nrt1.2B and their upstream regions are isolated as well. Any one of the sequences of SEQ ID No: 3 to 6 obtained in the Example corresponds to either of the upstream regions of nrt1.2A or nrt1.2B. However, whether the sequences of SEQ ID No: 3 to 6 correspond to the sequence of the upstream region of nrt1.2A or nrt1.2B is not determined in the Example.

Example 3

Expression Analysis of Low-Affinity Nitrate Transporter Genes (Part 1)

Tobacco seedlings grown for one month after seeding were cultivated by means of hydroponics, and the total RNA was extracted from flowers, laminas, midribs (main veins), stems and roots. Reverse transcription reaction was carried out using the total RNA as the template. More specifically, the reaction mixture containing 1 to 2 μg of the total RNA, 10×RT buffer, a final concentration of 0.5 mM of dNTPs, 10 pmol of oligo dT (15) primer, 10 units of an RNase inhibitor (Applied Biosystems), and 1 unit of Omniscript Reverse Transcriptase (Qiagen) was prepared in the total amount of 10 μL using RNase-free water. The resulting reaction mixture was subjected to reverse transcription reaction at 37° C. for 60 minutes, and then was treated at 93° C. for 5 minutes to inactivate the enzyme.

This reaction mixture was diluted 5-fold with sterilized water, and quantitative PCR was carried out using 5 μL of the diluted reaction mixture as a template by means of an ABI PRISM 7700 Sequence Detection System (Applied Biosystems). The quantitative PCR utilized a SYBR Green PCR Core Reagents Kit (Applied Biosystems) and was performed according to the protocol attached. As a primer set for genes to be quantified (low-affinity nitrate transporter genes) were employed a primer set specifically amplifying Group nrt1.1 and a primer set specifically amplifying Group nrt1.2. Also, a primer set specifically amplifying the ATP synthase gene was used as an internal standard. The nucleotide sequences of respective primers are as follows:

Primer Set for Group nrt1.1

F: 5'-AACGTTGAGTGTGTTGAATTTGAT-3'    (SEQ ID No: 27)

R: 5'-CTGGTTCTGAATCCTCCATTTC-3'    (SEQ ID No: 28)

Primer Set for Group nrt1.2

F: 5'-TGTTGTGACTGGGACAACAAATC-3'    (SEQ ID No: 29)

R: 5'-AATCCCCATTTCAGCAAGTCTCTT-3'    (SEQ ID No: 30)

Primer Set for ATP Synthase Gene

F: 5'-AAACGATTGCTCTGAAAGGTCATC-3'    (SEQ ID No: 31)

R: 5'-GCCCCTGGAAAGTATGTCGAC-3'    (SEQ ID No: 32)

The results are illustrated in FIG. 1. In FIG. 1, "F" represents a gene expression level (mRNA level) in a flower, "L" represents that in a lamina, "M" represents that in a midrib, S represents that in a stem, and R represents that in a root. In FIG. 1, the gene expression level (mRNA level) is shown by a relative value based on the amount of mRNA expression of the ATP synthase.

In Group nrt1.1, the expression in root was particularly high, but was uniformly expressed in other organs of a flower, lamina, midrib and stem. In Group nrt1.2, the expression was particularly high in root, and was also observed in stem and flower, but was rarely seen in lamina and midrib.

Example 4

Expression Analysis of Low-Affinity Nitrate Transporter Genes (Part 2)

Tobacco seedlings grown for one month after seeding were cultivated for 10 days in a hydroponic solution containing 10 mM nitrate, and further cultivated for 7 days in a solution containing 5 mM nitrate or nitrogen-free solution. Thereafter, the tobacco seedling that has been subjected to cultivation in the solution containing 5 mM nitrate was transferred to a nitrogen-free solution. A portion of the root was sampled after the lapse of a given period of cultivation in a nitrogen-free solution, and total RNA of the root was extracted. On the other hand, the tobacco seedling that has been subjected to cultivation in the nitrogen-free solution was transferred to a hydroponic solution containing 0.2 mM or 5 mM nitrate. A portion of the root was sampled after the lapse of a given period of cultivation in a hydroponic solution containing nitrate, and total RNA of the root was extracted.

In accordance with Example 2, the amounts of expression of Groups nrt1.1 and nrt1.2 were determined by means of quantitative RT-PCR. The results are shown in FIG. 2. FIG. 2A indicates the amount of expression of Group nrt1.1 and FIG. 2B indicates the amount of expression of Group nrt1.2. In FIGS. 2A and 2B, the expression "5 mM→0 mM" indicates the case where the tobacco seedling that has been subjected to cultivation in the hydroponic solution containing 5 mM nitrate was transferred to a nitrogen-free solution; the expression "0 mM→5 mM" indicates the case where the tobacco seedling that has been subjected to cultivation in the nitrogen-free solution was transferred to a hydroponic solution containing 5 mM nitrate; and the expression "0 mM→0.2 mM" indicates the case where the tobacco seedling that has been subjected to cultivation in the nitrogen-free solution was transferred to a hydroponic solution containing 0.2 mM nitrate. The transferred point is set to 0 hour; and the horizontal axis shows time (hours). The vertical axis indicates the ratio of Group nrt1.1 mRNA/ATP synthase mRNA in FIG. 2A, and indicates the ratio of Group nrt1.2 mRNA/ATP synthase mRNA in FIG. 2B.

The expression of Group nrt1.1 rarely changes even if the seedling is transferred to nitrogen-starved conditions; but the expression is induced within one hour after the addition of nitrate, and thereafter a high expression level is maintained (FIG. 2A). On the other hand, the expression of Group nrt1.2 rapidly decreases upon the change to nitrogen-starved conditions, and the addition of nitrate induces the expression within two hours after the addition (FIG. 2B).

Example 5

Measurement of Promoter Activity of Low-Affinity Nitrate Transporter Gene Using GUS Gene About 1.6 kb of the upstream region of the nrt1.1B gene (SEQ ID No: 15) was cloned, and a GUS gene was connected to the downstream of the cloned upstream region of the nrt1.1B gene. About 1.6 kb of the upstream region of the nrt1.1B gene was inserted into the upstream of the GUS gene contained in a binary vector pBI101.2 (Clonetech) such that the reading frame was conformed. The nucleotide sequence of the resulting vector was analyzed to confirm that the reading flame is precise, and then an *Agrobacterium tumefaciens* LBA4404 strain was transformed with the vector by electroporation. Transformants were selected using a culture medium containing 100 ppm kanamycin to obtain transformed strains. The resultant transformants were histologically subjected to GUS staining. More specifically, the sample of the transformant was immersed in a solution containing 1 mM 5-bromo-4-chloro-3-indolylglucuronide (X-Gluc), 50 mM phosphate buffer (pH 7.0) and 20% methanol to cause a reaction at 37° C. overnight. Thereafter, the resulting sample was washed with 100% methanol 2 to 3 times at intervals of two hours.

As a result, strong expression was detected in the cortex and the central cylinder of the root and the vascular bundle tissue of the leaf. The result suggests that the promoter of nrt1.1B is involved in the uptake of nitrate from the external environment in the root and in their transport from parenchyma to vessel in the root. Also, the result suggests that the promoter of nrt1.1B is involved in the transport of nitrate from vessel to mesophyll cells in the leaf.

Example 6

Transient Assay of Downstream Gene by Low-Affinity Nitrate Transporter Gene Promoter Using BY2 Cultured Cells (1) Preparation of Protoplasts of BY2 Culctured Cells BY2 cultured cells were inoculated into a medium (pH 5.8) containing 1×MS salt mixture, 200 mg/L KH$_2$PO$_4$, 100 mg/L myo-inositol, 1 mg/L thiamine chloride, 0.2 mg/L 2,4-D and 3% sucrose, cultured with shaking for 3 to 4 days, and then collected by precipitation. The supernatant was removed, 0.4 M mannitol was added to the precipitated cells, and the resulting cell suspension was allowed to stand at 30° C. for 10 minutes. The supernatant was removed, an enzyme solution (1% cellulase ONOZUKA RS, 0.1% pectriase Y23, 0.4 M mannitol) was added to the precipitated cells, and the resulting cell suspension was reacted at 30° C. for 1 to 2 hours. After the reaction, the cell suspension was transferred to a 50 mL centrifuge tube and centrifuged at 1000 rpm for 2 minutes. The supernatant was removed, and the precipitated cells were washed by centrifugal washing with 0.4 M ice-cooled mannitol at 6 times or more, and then the resulting cells were suspended in an MES-mannitol solution (0.3 M mannitol, 5 mM MES, 70 mM KCl, pH 5.8).

(2) Preparation of Deletion Promoter

A DNA fragment was prepared by connecting the GUS gene to about 3.3 kb of the upstream region of the nrt1.1A gene (SEQ ID No: 13), and inserted to the HindIII, EcoRI site of a pBluescript vector. The obtained vector was introduced into an *E. coli* TB1 strain to obtain large number of plasmid vectors. The plasmid vectors were treated with a Deletion Kit for Kilo-Sequence (TaKaRa) to obtain deletion series having promoter regions of different lengths. The plasmid vector was extracted from each clone, and subjected to sequencing to determine the length of the promoter region.

(3) Electroporation

The BY2 protoplasts prepared in (1) were adjusted to a concentration of 6×10$^6$/mL, and mixed with the plasmid vector prepared in (2). The amount of the vector used was 3 µg. A pBI121 containing a GUS gene (Clonetech) was used as a control. The mixture was cooled on ice for 5 minutes, and transferred to a 0.2 cm cuvette (available from Bio-Rad), and then subjected to a damped wave of 160 kV and 125 µF by means of Genepulser II (available from Bio-Rad). The resulting mixture was transferred into a tube, and allowed to stand 30 minutes on ice, and then treated at 30° C. for 5 minutes. After the centrifugation at 1000 rpm for 2 minutes, the precipitate was suspended in a protoplast culture medium (1×MS salt mixture, 100 mg/L myo-inositol, 1 mg/L thiamine chloride, 0.2 mg/L 2,4-D, 0.4 M mannitol, pH 5.8), and then cultured at 28° C. for 16 hours.

(4) Analysis of GUS Activity

The protoplasts obtained in (3) was collected by centrifuging at 1000 rpm for 2 minutes, and an extraction buffer (50 mM sodium phosphate buffer, pH 7.0, 1 mM Na$_2$EDTA, 0.1% Triton X-100, 0.1% sodium N-lauroylsarcosinate, 10 mM β-mercaptoethanol) was added thereto, and then the resulting mixture was sonicated with ultrasonic waves. The sonicated protoplasts were centrifuged at 15000 rpm at 4° C. for 15 minutes to obtain a supernatant.

4-Methylumbelliferyl glucuronide (MUG) was added to the sample such that the final concentration was 1 mM, and then the mixture was reacted at 37° C. for 30 minutes. Thereto was added 0.2 M sodium carbonate to stop the reaction, and then 4-methylumbelliferon (4-MU), which is a reaction product of the GUS enzyme, was determined by a fluorescence spectrometer (excitation wavelength 365 nm, emission wavelength 455 nm). A standard curve was described using 4-MU solutions of 200 nM to 1000 nM. The GUS enzyme activity was expressed in terms of a 4-MU amount per minute per milligram of protein.

The results are shown in Table 1.

TABLE 1

| Length of promoter region (bp) | GUS relative activity |
|---|---|
| 362 | 1.00 |
| 287 | 1.05 |
| 141 | 1.06 |
| 114 | 1.02 |
| 28 | 0.09 |
| −156 | 0 |

Table 1 shows the amounts of transient expression of the downstream GUS gene of deletion promoter introduced into BY2 protoplasts. In Table 1, the term "length of a promoter region (bp)" means the length of the upstream region from the translation initiation codon ATG (the initiation codon ATG is excluded). In addition, a minus value of the "length of a promoter region (bp)" indicates that the sequence of the downstream region from the initiation codon ATG is used as promoter. When the sequence of the upstream region from the initiation codon is used in the example as a deletion promoter, the sequence of SEQ ID No: 1 is referred to for its sequence. Also, when the sequence of the downstream region from the initiation codon was used as a deletion promoter, the sequence of SEQ ID No: 13 is referred to for its sequence. In Table 1, the term "GUS relative activity" is expressed as a relative value in the case where the GUS activity in pBI121 (control) is set up as 1.00.

The promoter activity was rarely changed even though the length of the promoter region had been shortened to 114 bp by deleting the promoter region. On the other hand, when the length of the promoter region had been shortened to 28 bp, the promoter activity extremely decreased. This shows that the TATA box is essential for the sequence of the upstream region of the low-affinity nitrate transporter gene to function as a promoter. In other words, in the sequence of the upstream region of the low-affinity nitrate transporter gene, the sequence from the TATA box to the initiation codon ATG (wherein the TATA box is included, but ATG is excluded) is estimated to be essential for the activity of the promoter.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An isolated promoter comprising the nucleotide sequence of SEQ ID NO: 7, wherein said promoter is capable of inducing the expression of a gene operably linked to the promoter under the presence of nitrate.

2. An expression vector containing the promoter according to claim 1.

3. An isolated cell having the expression vector of claim 2.

4. A transformed plant comprising the cell of claim 3.

5. A method of regulating in a cell the amount of expression of a gene operably linked to the promoter according to claim 1, said method comprising:
   providing a cell having an expression vector comprising the promoter of claim 1 operably linked to a gene; and
   regulating the concentration of nitrate in the environment in which the cell is placed.

6. A method of regulating in a plant the amount of expression of a coding sequence operably linked to the promoter according to claim 1, said method comprising:
   providing a plant comprising a cell having an expression vector, said expression vector comprising the promoter of claim 1 operably linked to a gene; and
   regulating the concentration of nitrate in the environment in which the plant is placed.

* * * * *

SEQUENCE LISTING

```
<160> NUMBER OF SEQ ID NOS: 32

<210> SEQ ID NO 1
<211> LENGTH: 703
<212> TYPE: DNA
<213> ORGANISM: Nicotiana tabacum
<220> FEATURE:
<221> NAME/KEY: TATA_signal
<222> LOCATION: (617)..(623)
<220> FEATURE:
<221> NAME/KEY: 5'UTR
<222> LOCATION: (648)..(703)

<400> SEQUENCE: 1
ccacaaaaag atgaaaatta attttgttac ttaggggcgg aggccatttt tatccacaaa      60
tatctcaaca catactctaa atcactttct ttgaccattc aaacactggt gtcaatttct     120
aatactcaga ataatcatca aacacttcta ccgtcttact ctattcttca cctcgtgtaa     180
ttatcatata tcgcctaatc ctatacgaac caaatattgg cataaatgat ctagattttc     240
caaggtgaac atttgctaaa aaattgcttt tctccttaat ataacacgtt taaagggata     300
tttaaatgac taattttatt ttcttaaact aaaggtgtaa tccctttta attaccacag      360 actaagcact ttttccttct ttcaagttca tgggtacagg catctagcag ttcactgtca     420
atcattttgt gtatcatttg aggctaggga ccacgaaatt tcttgtatta aaaaaaaaa     480 ggaaaatcaa aataaggaaa agacaatcat gtggacttac cactcccttc gataatggac     540
ctaagtagaa taaaaaaata tagatattaa aataataaaa aattaaaaac acaggagtta     600
accccaaacc tacggctata aaagggtaat ggaatcaatt gaatcttacc atagtcttgg     660
ataccttttc ctctgcaacc tttttttctt attatcgttc aaa                       703

<210> SEQ ID NO 2
<211> LENGTH: 969
<212> TYPE: DNA
<213> ORGANISM: Nicotiana tabacum
<220> FEATURE:
<221> NAME/KEY: TATA_signal
<222> LOCATION: (821)..(827)
<220> FEATURE:
<221> NAME/KEY: 5'UTR
<222> LOCATION: (852)..(969)

<400> SEQUENCE: 2
taatacaaat atatatagag tttacgcaaa agctactgag ttcatccgaa cccgtaacta      60
atgtttttcc tccgcccctg ttactccata tgttttaagg tgttttggtg gcgctaaatg     120
```

-continued

```
ttatcccaaa gtatattttc ttgaaatatg ttattttttga tgagatcatt ttctagtaga      180
gtatttggtt actatgatcc aagaaaaacg ttacaacaaa aagatgaaaa tttatttttt      240
ttacttaggg gcggaggtca ttttttatcca caaatatctc aactcataat ctatatcact      300
ttctttgacc attctaacat tgttgtcaat ttctaatact cagaaatatc atcaagcaca      360
accttcgtac tctattcttc acctgtaatt atcatatatc gcataatcct ctacggacca      420
aacattggca taaatgatct agattttcca aggtaaaaca tttgctatag aaatgctttc      480
ctccttaata taacacgttt aaagggatat ttaaatggct aatttgattt cataaactaa      540
aggtgtaatc ctttttttaat taccagagag gcagagacta ggcactttt ccttctttca      600 agttcgtggg tacaggcatc tagcagttca ctgtcaatca ttttgtgtat catttgaggc      660
tagggaccac gaaatttctt agttaaaaaa aataaatcaa ataaggaaa agacaataat      720 gtggacttac cactcccttt gataatggac ctaagtagaa taaaaaaata taggtattaa      780
aataatcaaa aaagcacagg agttacccca aacctacggc tataaagggg taatggaatc      840
aattgaatct taccatactc ttggatacct tttctatctc ctaatatctc aaactcctct      900
tcaacctttt tttcttatcg ttcaaataca ccattgaaac acaaacttaa caaaaggtc      960 tagctaaaa                                                               969

<210> SEQ ID NO 3
<211> LENGTH: 1063
<212> TYPE: DNA
<213> ORGANISM: Nicotiana tabacum
<220> FEATURE:
<221> NAME/KEY: TATA_signal
<222> LOCATION: (941)..(947)
<220> FEATURE:
<221> NAME/KEY: 5'UTR
<222> LOCATION: (973)..(1063)

<400> SEQUENCE: 3
tttcccgggc cagaaaagtt acattctgta tacaaatgta atggatcccc atcacctatt       60
attgatggct atatttactc tcaagattcc gataagtcaa taaaatcttg tgatatacat      120
ggttgcaaca atgagtcttc ttgcttagag gccttaggct caagtcccgg gaatagaaaa      180
atcctgatat gaaacgcgtc cctctttaat aagtcttatg ggcgtgaatc taaattagtc      240 gatacccccac gacgaatatc atggtgaaaa atatattttt ttccactagc ttggttgatt      300
acgagcaata gataacagat actattatta gagtaggcta tttatatcaa tgccttaaag      360
tgcgatcctt cccgaaattc cgagtgaatg cggaatactt tatgcaccgc acttctatta      420
tttagataat agatacactt ctgacttttta tttatcattg gcctttattt aggtacaact      480
tttatcattc agaataccac atcaataata ataataataa taataataat aataataata      540
ataataatca ttgcagctct ttgaatcagc tatatgaatt ctcattcact ttggttaaat      600
ttatcacagt taatattata caacaaaaag gtactccgac gattattaaa agtgattaaa      660
atgctaaatt atacttaggg tatgccaaat tcacttttac aagctaatta gagtaagaat      720
tcatgtgcat aaataagaat agaagttaat caaattacaa tcaatcattt tctgtagcat      780
ttgatgctgt ggacaacttc tcatccaaca aaaaagaaa aaaggaaag acagtcctgg      840 ggagttgtta ctaccattga agtggacca tgtggaataa aatatttttg tgtaataaaa      900
aatggctaaa aatgcaattg agttgcccct aggccatggc tataaagggg taatggaatc      960
aattgaatct gcaatcttct tctagttttt ccatattaac cttttttttct cattgttcat     1020 tgggtccatt tttgtgggca aaagtgcaag aaaagttgct aaa                        1063
```

<210> SEQ ID NO 4
<211> LENGTH: 828
<212> TYPE: DNA
<213> ORGANISM: Nicotiana tabacum
<220> FEATURE:
<221> NAME/KEY: TATA_signal
<222> LOCATION: (704)..(710)
<220> FEATURE:
<221> NAME/KEY: 5'UTR
<222> LOCATION: (736)..(828)

<400> SEQUENCE: 4

```
ccatgtaaat tatttgatac ggttcagtat tttttaggtt ttattttcgt agaataaaaa      60
acctatccta attatcggta cggttataga tttatataaa aacctacggg ttttattaaa     120
agaaacctaa aaatcggttc ggttcgggta cgggtacggt tcggccgatt tagtcgattt     180
ttaaatatcc attgacaccc ctagtagata cccttgtgaa ttttgtttac gattaatttt     240
tatttaggta aacttttat catcagccag aatatcgcat caataataac aatcagcacc      300
tcaatccaag taaatttgat taatggacta tatgaattca cacccatcat gtctctctca     360
tggaccaata ttatacaaaa agagagaggg tactttccaa cgattattaa aagtgattaa     420
aatggtaaaa ctatacttag ggtatgccaa attcactttt acaaggtaaa tagagtaaga     480
gttcatgtgc atgtataagg atagaagtta gtcaaattac aatcaatcat tttctgtagc     540
atttgatgct gtggacaact ctctcatcca caaaaaaaag aaaaaaagga aagacaatcc     600
tggggagttg ctactgccat tgatagtgga ccatgtggaa taaatatttt tggtgtatta     660
aaaaatggct aaaatgcaa ttgagttgcc tctaggccat ggctataaaa gggtaatgga     720
atcaattgaa tctgcaatct tcttctagtt tttccatatt aacctttttt tttctcattg     780
ctcattgggt ccattttgt gggcaaaagt gcaagaaaag ttgctaaa                  828
```

<210> SEQ ID NO 5
<211> LENGTH: 932
<212> TYPE: DNA
<213> ORGANISM: Nicotiana tabacum
<220> FEATURE:
<221> NAME/KEY: TATA_signal
<222> LOCATION: (810)..(816)
<220> FEATURE:
<221> NAME/KEY: 5'UTR
<222> LOCATION: (835)..(932)

<400> SEQUENCE: 5

```
aatttgtctt ttctgatgat tgaaaaatta taagaaaggc caccatttaa taggcgcctt      60
gatcataaga gttatttaaa actagtattt ttttattta aatgcttacg taattaatat     120
tttcctaatt aaaccaataa gaaactatga attgattcta aaccaatttt attaataacc     180
tcgtattttt cttaattaaa tgtcatcaaa gaattcactt cgccacaatg aactaccatt     240
atttagataa tagatacact tgtgactttt atttatcatt ggtctttatt tagatacatc     300
ttttatcatt cagcatacca caataataat aataataata ataataataa taataataat     360
aataataata ataataatca tcatcatctt tgcatctcaa tcccaagtaa atttgaatcg     420
gcaatatgaa ttctcactcg tcatatcact tggttaaat ttatcacagt caatattata     480
caacaaaaaa gttactccaa cgattattaa aagtgattaa aatgctaaaa ctatacttag     540
ggtatgccaa attcactttt acaaggtaat tagagtaaga attcatgtgc atgaataaga     600
atagaagtta gtcaaattac aatcaaccat tttctgtagc atttgatgct gtggacaact     660
```

-continued

```
tctcattcaa caaaaaagaa aaaagaaaa aaaggaaaga caatcctggg gagttgctac    720
tgccattgaa agtggaccat gtggaataaa atatttttgt gcattaaaaa atggctaaaa    780
atgcaattga gttgcctcta ggccatggct ataaaagggt aatggaatca attgaatctg    840
caatcttctt ctagttttttc catattaacc ttttttttctt attgctcatt gggtccattt    900
ttgtgggcaa tagtgcaaga aaagttgcaa aa                                  932
```

<210> SEQ ID NO 6
<211> LENGTH: 1138
<212> TYPE: DNA
<213> ORGANISM: Nicotiana tabacum
<220> FEATURE:
<221> NAME/KEY: TATA_signal
<222> LOCATION: (1009)..(1015)
<220> FEATURE:
<221> NAME/KEY: 5'UTR
<222> LOCATION: (1035)..(1138)

<400> SEQUENCE: 6

```
atttaatcgc taagcaacaa ataatcatgt aggtgcaaat ttcctggggc cagaaaatta    60
aagttactat tctgtataca aatgtaatag aaattatatt gcatgttctg atgttgatac   120
ccatcaccca ttattgatag ctatatttac tctcaagatt ccgataagtg tacaaaatct   180
tgtgatatac gtggtcgcaa caatgagtct tcttgcttag aggccttagg ctcgagtccc   240
gggaatagaa tgatcctgat atggaacgtg tctttcttta ataagtctta tgggcgtgaa   300
tctaattaaa ttagtctatg ccctacgaca aatatcgtgg tgaaaaaata tatttttttc   360
ccactagctt ggtgattacg ctcaatagat aagagatact atatttcgag taggctacct   420
gctacctaca tcagaccctc ttagagtgca acactttccc gaatcgtgag tgaacgcgaa   480
atgttttatg caccgcactg ccattattta gataatagat gcacttgtct ttatttaggt   540
acaactttta tcatttagaa taccacatca ataataataa taataattgc agctcaatcc   600
caagtaaatt tgaatcggct atataaagat tcactcatca tctcactttg gttaaattaa   660
tcacagtcaa tattatacaa caaaaaaaag gtactccaac gattattaaa agtgattaaa   720
atgctaaaac tatacttagg gtatgccaaa ttcacttttta caaggtaatt agagtaagaa   780
ttcatgtgca taaataagaa tagaagttag tcaaattaca atcaatcatt ttctgtagca   840
tttgatgctg tggacaactt ctcatccaac aaaaaagata aagaaaaaa aggaaagaca   900 atcctgggga gttgctactg ccattgaaag tggaccatgt ggaataaaat atttttgtg   960 tattaaaaaa tggctaaaaa tgcaattgag ttgcctctag gccatggcta taaagggta  1020 atggaatcaa agtgaatctg caatcttctt ctagttttttc catattaacc tctctttttt  1080
ctctcattgc tcattgggtc caattttttgt gggcaaaagt gcaagaaaag ttgctaaa    1138
```

<210> SEQ ID NO 7
<211> LENGTH: 87
<212> TYPE: DNA
<213> ORGANISM: Nicotiana tabacum
<220> FEATURE:
<221> NAME/KEY: TATA_signal
<222> LOCATION: (1)..(7)
<220> FEATURE:
<221> NAME/KEY: 5'UTR
<222> LOCATION: (32)..(87)

<400> SEQUENCE: 7

```
tataaaaggg taatggaatc aattgaatct taccatagtc ttggatacct tttcctctgc    60
aacctttttt tcttattatc gttcaaa                                        87
```

<210> SEQ ID NO 8
<211> LENGTH: 149
<212> TYPE: DNA
<213> ORGANISM: Nicotiana tabacum
<220> FEATURE:
<221> NAME/KEY: TATA_signal
<222> LOCATION: (1)..(7)
<220> FEATURE:
<221> NAME/KEY: 5'UTR
<222> LOCATION: (32)..(149)

<400> SEQUENCE: 8 tataaaggg taatggaatc aattgaatct taccatactc ttggatacct tttctatctc     60
ctaatatctc aaactcctct tcaacctttt tttcttatcg ttcaaataca ccattgaaac    120
acaaacttaa caaaaaggtc tagctaaaa                                      149

<210> SEQ ID NO 9
<211> LENGTH: 123
<212> TYPE: DNA
<213> ORGANISM: Nicotiana tabacum
<220> FEATURE:
<221> NAME/KEY: TATA_signal
<222> LOCATION: (1)..(7)
<220> FEATURE:
<221> NAME/KEY: 5'UTR
<222> LOCATION: (33)..(123)

<400> SEQUENCE: 9 tataaaggg taatggaatc aattgaatct gcaatcttct tctagttttt ccatattaac     60 cttttttttct cattgttcat tgggtccatt tttgtgggca aaagtgcaag aaaagttgct  120
aaa                                                                 123

<210> SEQ ID NO 10
<211> LENGTH: 125
<212> TYPE: DNA
<213> ORGANISM: Nicotiana tabacum
<220> FEATURE:
<221> NAME/KEY: TATA_signal
<222> LOCATION: (1)..(7)
<220> FEATURE:
<221> NAME/KEY: 5'UTR
<222> LOCATION: (33)..(125)

<400> SEQUENCE: 10 tataaaggg taatggaatc aattgaatct gcaatcttct tctagttttt ccatattaac     60
cttttttttt ctcattgctc attgggtcca tttttgtggg caaaagtgca agaaaagttg  120
ctaaa                                                               125

<210> SEQ ID NO 11
<211> LENGTH: 123
<212> TYPE: DNA
<213> ORGANISM: Nicotiana tabacum
<220> FEATURE:
<221> NAME/KEY: TATA_signal
<222> LOCATION: (1)..(7)
<220> FEATURE:
<221> NAME/KEY: 5'UTR
<222> LOCATION: (26)..(123)

<400> SEQUENCE: 11 tataaaggg taatggaatc aattgaatct gcaatcttct tctagttttt ccatattaac     60 cttttttct tattgctcat tgggtccatt tttgtgggca aatagtgcaag aaaagttgca  120

-continued

```
                                                                    aaa                                                               123

<210> SEQ ID NO 12
<211> LENGTH: 130
<212> TYPE: DNA
<213> ORGANISM: Nicotiana tabacum
<220> FEATURE:
<221> NAME/KEY: TATA_signal
<222> LOCATION: (1)..(7)
<220> FEATURE:
<221> NAME/KEY: 5'UTR
<222> LOCATION: (27)..(130)

<400> SEQUENCE: 12 tataaaggg taatggaatc aaagtgaatc tgcaatcttc ttctagtttt tccatattaa     60
cctctctttt ttctctcatt gctcattggg tccaattttt gtgggcaaaa gtgcaagaaa    120
agttgctaaa                                                          130

<210> SEQ ID NO 13
<211> LENGTH: 1773
<212> TYPE: DNA
<213> ORGANISM: Nicotiana tabacum
<220> FEATURE:
<221> NAME/KEY: CDS
<222> LOCATION: (1)..(1770)

<400> SEQUENCE: 13
```

| | | | | | | | | | | | | | | | | |
|---|---|---|---|---|---|---|---|---|---|---|---|---|---|---|---|---|
| atg | gca | ctt | cct | gaa | aca | caa | caa | gat | act | aaa | act | ctc | cca | gat | gcc | 48 |
| Met | Ala | Leu | Pro | Glu | Thr | Gln | Gln | Asp | Thr | Lys | Thr | Leu | Pro | Asp | Ala | |
| 1 | | | | 5 | | | | | 10 | | | | | 15 | | |
| tgg | gat | tac | aaa | ggt | cga | cca | gct | gtt | cgt | tcc | tcg | tcc | ggc | ggt | tgg | 96 |
| Trp | Asp | Tyr | Lys | Gly | Arg | Pro | Ala | Val | Arg | Ser | Ser | Ser | Gly | Gly | Trp | |
| | | | 20 | | | | | 25 | | | | | 30 | | | |
| tcc | agc | gcc | gcc | atg | att | tta | ggg | att | gag | gca | gtg | gag | agg | ctg | acg | 144 |
| Ser | Ser | Ala | Ala | Met | Ile | Leu | Gly | Ile | Glu | Ala | Val | Glu | Arg | Leu | Thr | |
| | | 35 | | | | | 40 | | | | | 45 | | | | |
| acg | tta | ggt | att | gct | gta | aat | ctg | gtg | aca | tat | ttg | act | gga | acc | atg | 192 |
| Thr | Leu | Gly | Ile | Ala | Val | Asn | Leu | Val | Thr | Tyr | Leu | Thr | Gly | Thr | Met | |
| | 50 | | | | | 55 | | | | | 60 | | | | | |
| cat | tta | gga | aat | gct | agt | tcg | gcc | aac | aat | gtt | act | aat | ttt | ctt | gga | 240 |
| His | Leu | Gly | Asn | Ala | Ser | Ser | Ala | Asn | Asn | Val | Thr | Asn | Phe | Leu | Gly | |
| 65 | | | | | 70 | | | | | 75 | | | | | 80 | |
| act | tca | ttt | atg | ctc | act | ttg | ctt | ggt | ggt | ttc | gta | gcc | gac | act | ttt | 288 |
| Thr | Ser | Phe | Met | Leu | Thr | Leu | Leu | Gly | Gly | Phe | Val | Ala | Asp | Thr | Phe | |
| | | | | 85 | | | | | 90 | | | | | 95 | | |
| ctt | gga | cgg | tat | ctt | aca | att | ggt | atc | ttt | acc | act | att | caa | gcc | atg | 336 |
| Leu | Gly | Arg | Tyr | Leu | Thr | Ile | Gly | Ile | Phe | Thr | Thr | Ile | Gln | Ala | Met | |
| | | | 100 | | | | | 105 | | | | | 110 | | | |
| ggt | gtt | acc | ata | ttg | acc | atc | tcc | acc | ata | atc | cca | agc | cta | cga | cca | 384 |
| Gly | Val | Thr | Ile | Leu | Thr | Ile | Ser | Thr | Ile | Ile | Pro | Ser | Leu | Arg | Pro | |
| | | | 115 | | | | | 120 | | | | | 125 | | | |
| cca | aag | tgt | tcc | cca | ggg | agc | tca | aca | tgc | att | cca | gca | agt | tcc | aaa | 432 |
| Pro | Lys | Cys | Ser | Pro | Gly | Ser | Ser | Thr | Cys | Ile | Pro | Ala | Ser | Ser | Lys | |
| | 130 | | | | | 135 | | | | | 140 | | | | | |
| caa | ctc | atg | gtt | cta | tac | ata | gca | cta | tac | atg | acg | gcg | ctc | ggc | acc | 480 |
| Gln | Leu | Met | Val | Leu | Tyr | Ile | Ala | Leu | Tyr | Met | Thr | Ala | Leu | Gly | Thr | |
| 145 | | | | | 150 | | | | | 155 | | | | | 160 | |
| ggc | ggc | ctg | aaa | tcc | agc | gtc | tcc | ggc | ttc | ggt | tcc | gat | caa | ttc | gac | 528 |
| Gly | Gly | Leu | Lys | Ser | Ser | Val | Ser | Gly | Phe | Gly | Ser | Asp | Gln | Phe | Asp | |
| | | | | 165 | | | | | 170 | | | | | 175 | | |
| gaa | acc | gac | aag | aaa | gaa | aga | gga | cag | atg | ata | aaa | ttc | ttc | aac | tgg | 576 |
| Glu | Thr | Asp | Lys | Lys | Glu | Arg | Gly | Gln | Met | Ile | Lys | Phe | Phe | Asn | Trp | |

|  |  |  |  |  |  |  |  |  |  |  |  |  |  |  |  |
|---|---|---|---|---|---|---|---|---|---|---|---|---|---|---|---|
| ttc | ttt | ttc | ttc | att | aac | gtg | gga | tcc | ctt | ggt | gca | gtg | aca | gta | cta | 624 |
| Phe | Phe | Phe | Phe | Ile | Asn | Val | Gly | Ser | Leu | Gly | Ala | Val | Thr | Val | Leu | |
|  |  | 195 |  |  |  | 200 |  |  |  | 205 |  |  |  |  |  |

| gtg | tat | att | caa | gat | aat | ttg | gga | aga | gaa | tat | ggt | tat | gga | ata | tgt | 672 |
| Val | Tyr | Ile | Gln | Asp | Asn | Leu | Gly | Arg | Glu | Tyr | Gly | Tyr | Gly | Ile | Cys | |
| 210 | | | | | 215 | | | | | 220 | | | | | | |

| gct | tgt | gct | att | gtt | att | ggt | ttg | gtc | ata | ttc | tta | tcg | ggc | aca | aga | 720 |
| Ala | Cys | Ala | Ile | Val | Ile | Gly | Leu | Val | Ile | Phe | Leu | Ser | Gly | Thr | Arg | |
| 225 | | | | | 230 | | | | | 235 | | | | | 240 | |

| aaa | tat | cgt | ttc | aag | aaa | ctt | gtg | gga | agt | cca | ttg | aca | caa | att | gct | 768 |
| Lys | Tyr | Arg | Phe | Lys | Lys | Leu | Val | Gly | Ser | Pro | Leu | Thr | Gln | Ile | Ala | |
| | | | | 245 | | | | | 250 | | | | | 255 | | |

| tca | gtt | ttt | gtg | gct | gct | tgg | aac | aaa | aga | cat | atg | gat | ttg | cct | tct | 816 |
| Ser | Val | Phe | Val | Ala | Ala | Trp | Asn | Lys | Arg | His | Met | Asp | Leu | Pro | Ser | |
| | | | | 260 | | | | | 265 | | | | | 270 | | |

| gat | tct | tat | ctt | cta | tat | aat | att | gat | gat | att | cct | ggg | gat | gga | aat | 864 |
| Asp | Ser | Tyr | Leu | Leu | Tyr | Asn | Ile | Asp | Asp | Ile | Pro | Gly | Asp | Gly | Asn | |
| | | 275 | | | | | 280 | | | | | 285 | | | | |

| aaa | aaa | gct | aag | cag | aga | ttg | cct | cac | agc | aag | gaa | ttc | cgt | ttc | ttg | 912 |
| Lys | Lys | Ala | Lys | Gln | Arg | Leu | Pro | His | Ser | Lys | Glu | Phe | Arg | Phe | Leu | |
| | 290 | | | | | 295 | | | | | 300 | | | | | |

| gac | aag | gca | gct | att | aaa | gta | cag | gac | cct | gaa | tcc | gct | gga | att | acc | 960 |
| Asp | Lys | Ala | Ala | Ile | Lys | Val | Gln | Asp | Pro | Glu | Ser | Ala | Gly | Ile | Thr | |
| 305 | | | | | 310 | | | | | 315 | | | | | 320 | |

| gtg | gta | aat | aaa | tgg | aac | tta | tca | act | tta | acc | gac | gtt | gaa | gaa | gta | 1008 |
| Val | Val | Asn | Lys | Trp | Asn | Leu | Ser | Thr | Leu | Thr | Asp | Val | Glu | Glu | Val | |
| | | | | 325 | | | | | 330 | | | | | 335 | | |

| aaa | ttg | gta | gtc | cga | atg | tta | cca | aca | tgg | gcc | acg | acc | att | atg | ttt | 1056 |
| Lys | Leu | Val | Val | Arg | Met | Leu | Pro | Thr | Trp | Ala | Thr | Thr | Ile | Met | Phe | |
| | | | 340 | | | | | 345 | | | | | 350 | | | |

| tgg | act | gtc | tat | gct | caa | atg | aca | aca | ttt | tca | gtg | tca | caa | gct | aca | 1104 |
| Trp | Thr | Val | Tyr | Ala | Gln | Met | Thr | Thr | Phe | Ser | Val | Ser | Gln | Ala | Thr | |
| | | 355 | | | | | 360 | | | | | 365 | | | | |

| aca | atg | gac | cgt | cac | atc | gga | aat | ttc | gaa | att | cct | ccg | gcc | tca | ttg | 1152 |
| Thr | Met | Asp | Arg | His | Ile | Gly | Asn | Phe | Glu | Ile | Pro | Pro | Ala | Ser | Leu | |
| 370 | | | | | 375 | | | | | 380 | | | | | | |

| aca | ctt | ttc | ttc | gtc | gga | agt | atc | ctc | tta | acg | tgc | ata | ttc | tac | gac | 1200 |
| Thr | Leu | Phe | Phe | Val | Gly | Ser | Ile | Leu | Leu | Thr | Cys | Ile | Phe | Tyr | Asp | |
| 385 | | | | | 390 | | | | | 395 | | | | | 400 | |

| cgt | gcc | gtc | gta | ccg | gtt | tgt | cga | cgt | gtc | cta | aac | aat | cct | cac | ggt | 1248 |
| Arg | Ala | Val | Val | Pro | Val | Cys | Arg | Arg | Val | Leu | Asn | Asn | Pro | His | Gly | |
| | | | | 405 | | | | | 410 | | | | | 415 | | |

| aca | acc | ccg | ttg | caa | cgt | att | gca | gtt | gga | tta | ata | ctt | tca | att | ata | 1296 |
| Thr | Thr | Pro | Leu | Gln | Arg | Ile | Ala | Val | Gly | Leu | Ile | Leu | Ser | Ile | Ile | |
| | | | 420 | | | | | 425 | | | | | 430 | | | |

| gcc | atg | gtt | gct | gct | gct | tta | act | gaa | gtg | aag | aga | ttg | aat | gtt | gca | 1344 |
| Ala | Met | Val | Ala | Ala | Ala | Leu | Thr | Glu | Val | Lys | Arg | Leu | Asn | Val | Ala | |
| | | 435 | | | | | 440 | | | | | 445 | | | | |

| cat | ttg | cat | gga | ttg | acc | aat | gat | gca | aat | gcc | aag | gtt | cct | ttg | agt | 1392 |
| His | Leu | His | Gly | Leu | Thr | Asn | Asp | Ala | Asn | Ala | Lys | Val | Pro | Leu | Ser | |
| 450 | | | | | 455 | | | | | 460 | | | | | | |

| gtt | ttt | tgg | tta | gtt | ccg | caa | ttc | ttg | cta | gta | ggg | gca | ggt | gag | gca | 1440 |
| Val | Phe | Trp | Leu | Val | Pro | Gln | Phe | Leu | Leu | Val | Gly | Ala | Gly | Glu | Ala | |
| 465 | | | | | 470 | | | | | 475 | | | | | 480 | |

| ttt | act | tat | atc | gga | caa | ctt | gat | ttc | ttc | cta | agg | gag | tgt | cct | aaa | 1488 |
| Phe | Thr | Tyr | Ile | Gly | Gln | Leu | Asp | Phe | Phe | Leu | Arg | Glu | Cys | Pro | Lys | |
| | | | | 485 | | | | | 490 | | | | | 495 | | |

| gga | atg | aag | aca | atg | agc | acg | ggg | tta | ttc | ttg | agt | aca | ctt | tca | tta | 1536 |

```
Gly Met Lys Thr Met Ser Thr Gly Leu Phe Leu Ser Thr Leu Ser Leu
            500                 505                 510 ggg ttt ttc ttt agt tct att ttg gtg act ata gtg cat aag gtg aca    1584
Gly Phe Phe Phe Ser Ser Ile Leu Val Thr Ile Val His Lys Val Thr
            515                 520                 525 gtg aaa aac cca tgg tta gct gat aat tta aac caa gga aga ctc tat    1632
Val Lys Asn Pro Trp Leu Ala Asp Asn Leu Asn Gln Gly Arg Leu Tyr
            530                 535                 540 gat ttc tat tgg cta ttg gca acg ttg agt gtg ttg aat ttg atg att    1680
Asp Phe Tyr Trp Leu Leu Ala Thr Leu Ser Val Leu Asn Leu Met Ile
545                 550                 555                 560 ttc ttg ttt att tca aga cgg tat gtg tac aag gag aag aga ctt gct    1728
Phe Leu Phe Ile Ser Arg Arg Tyr Val Tyr Lys Glu Lys Arg Leu Ala
                565                 570                 575 gaa tgt ggg att gaa atg gag gat tca gaa cca gct tgc cac taa        1773
Glu Cys Gly Ile Glu Met Glu Asp Ser Glu Pro Ala Cys His
            580                 585                 590

<210> SEQ ID NO 14
<211> LENGTH: 590
<212> TYPE: PRT
<213> ORGANISM: Nicotiana tabacum

<400> SEQUENCE: 14

Met Ala Leu Pro Glu Thr Gln Gln Asp Thr Lys Thr Leu Pro Asp Ala
1               5                   10                  15

Trp Asp Tyr Lys Gly Arg Pro Ala Val Arg Ser Ser Gly Gly Trp
            20                  25                  30

Ser Ser Ala Ala Met Ile Leu Gly Ile Glu Ala Val Glu Arg Leu Thr
            35                  40                  45

Thr Leu Gly Ile Ala Val Asn Leu Val Thr Tyr Leu Thr Gly Thr Met
        50                  55                  60

His Leu Gly Asn Ala Ser Ser Ala Asn Asn Val Thr Asn Phe Leu Gly
65                  70                  75                  80

Thr Ser Phe Met Leu Thr Leu Leu Gly Gly Phe Val Ala Asp Thr Phe
                85                  90                  95

Leu Gly Arg Tyr Leu Thr Ile Gly Ile Phe Thr Thr Ile Gln Ala Met
                100                 105                 110

Gly Val Thr Ile Leu Thr Ile Ser Thr Ile Ile Pro Ser Leu Arg Pro
            115                 120                 125

Pro Lys Cys Ser Pro Gly Ser Ser Thr Cys Ile Pro Ala Ser Ser Lys
            130                 135                 140

Gln Leu Met Val Leu Tyr Ile Ala Leu Tyr Met Thr Ala Leu Gly Thr
145                 150                 155                 160

Gly Gly Leu Lys Ser Ser Val Ser Gly Phe Gly Ser Asp Gln Phe Asp
                165                 170                 175

Glu Thr Asp Lys Lys Glu Arg Gly Gln Met Ile Lys Phe Phe Asn Trp
                180                 185                 190

Phe Phe Phe Phe Ile Asn Val Gly Ser Leu Gly Ala Val Thr Val Leu
            195                 200                 205

Val Tyr Ile Gln Asp Asn Leu Gly Arg Glu Tyr Gly Tyr Gly Ile Cys
        210                 215                 220

Ala Cys Ala Ile Val Ile Gly Leu Val Ile Phe Leu Ser Gly Thr Arg
225                 230                 235                 240

Lys Tyr Arg Phe Lys Lys Leu Val Gly Ser Pro Leu Thr Gln Ile Ala
                245                 250                 255
```

```
Ser Val Phe Val Ala Ala Trp Asn Lys Arg His Met Asp Leu Pro Ser
            260                 265                 270

Asp Ser Tyr Leu Leu Tyr Asn Ile Asp Asp Ile Pro Gly Asp Gly Asn
        275                 280                 285

Lys Lys Ala Lys Gln Arg Leu Pro His Ser Lys Glu Phe Arg Phe Leu
    290                 295                 300

Asp Lys Ala Ala Ile Lys Val Gln Asp Pro Glu Ser Ala Gly Ile Thr
305                 310                 315                 320

Val Val Asn Lys Trp Asn Leu Ser Thr Leu Thr Asp Val Glu Glu Val
            325                 330                 335

Lys Leu Val Val Arg Met Leu Pro Thr Trp Ala Thr Thr Ile Met Phe
        340                 345                 350

Trp Thr Val Tyr Ala Gln Met Thr Thr Phe Ser Val Ser Gln Ala Thr
    355                 360                 365

Thr Met Asp Arg His Ile Gly Asn Phe Glu Ile Pro Pro Ala Ser Leu
370                 375                 380

Thr Leu Phe Phe Val Gly Ser Ile Leu Leu Thr Cys Ile Phe Tyr Asp
385                 390                 395                 400

Arg Ala Val Val Pro Val Cys Arg Arg Val Leu Asn Asn Pro His Gly
            405                 410                 415

Thr Thr Pro Leu Gln Arg Ile Ala Val Gly Leu Ile Leu Ser Ile Ile
        420                 425                 430

Ala Met Val Ala Ala Leu Thr Glu Val Lys Arg Leu Asn Val Ala
    435                 440                 445

His Leu His Gly Leu Thr Asn Asp Ala Asn Ala Lys Val Pro Leu Ser
    450                 455                 460

Val Phe Trp Leu Val Pro Gln Phe Leu Leu Val Gly Ala Gly Glu Ala
465                 470                 475                 480

Phe Thr Tyr Ile Gly Gln Leu Asp Phe Phe Leu Arg Glu Cys Pro Lys
            485                 490                 495

Gly Met Lys Thr Met Ser Thr Gly Leu Phe Leu Ser Thr Leu Ser Leu
        500                 505                 510

Gly Phe Phe Phe Ser Ser Ile Leu Val Thr Ile Val His Lys Val Thr
    515                 520                 525

Val Lys Asn Pro Trp Leu Ala Asp Asn Leu Asn Gln Gly Arg Leu Tyr
530                 535                 540

Asp Phe Tyr Trp Leu Leu Ala Thr Leu Ser Val Leu Asn Leu Met Ile
545                 550                 555                 560

Phe Leu Phe Ile Ser Arg Arg Tyr Val Tyr Lys Glu Lys Arg Leu Ala
            565                 570                 575

Glu Cys Gly Ile Glu Met Glu Asp Ser Glu Pro Ala Cys His
        580                 585                 590

<210> SEQ ID NO 15
<211> LENGTH: 1773
<212> TYPE: DNA
<213> ORGANISM: Nicotiana tabacum
<220> FEATURE:
<221> NAME/KEY: CDS
<222> LOCATION: (1)..(1770)

<400> SEQUENCE: 15 atg gca ctt cct gaa aca caa caa gat aca aaa act ctc cca gat gcc      48
Met Ala Leu Pro Glu Thr Gln Gln Asp Thr Lys Thr Leu Pro Asp Ala
1               5                   10                  15 tgg gat tac aaa ggt cga cca gct gtt cga tcc tcg tcc ggc ggt tgg      96
```

|                                                                                  |      |
| -------------------------------------------------------------------------------- | ---- |
| Trp Asp Tyr Lys Gly Arg Pro Ala Val Arg Ser Ser Ser Gly Gly Trp                  |      |
|  20              25              30                                              |      |
| tcc agc gcc gcc atg att tta ggg att gag gca gtg gag agg cta acg                  | 144  |
| Ser Ser Ala Ala Met Ile Leu Gly Ile Glu Ala Val Glu Arg Leu Thr                  |      |
|      35              40              45                                          |      |
| acg tta ggt att gct gta aat ctg gtg aca tac ttg act gga acc atg                  | 192  |
| Thr Leu Gly Ile Ala Val Asn Leu Val Thr Tyr Leu Thr Gly Thr Met                  |      |
|  50              55              60                                              |      |
| cat tta gga aat gct agt tcg gcc aac aac gtt aca aat ttt ctt gga                  | 240  |
| His Leu Gly Asn Ala Ser Ser Ala Asn Asn Val Thr Asn Phe Leu Gly                  |      |
| 65              70              75              80                               |      |
| act tca ttt atg ctc act ttg ctt ggt ggt ttc gta gcc gac act ttt                  | 288  |
| Thr Ser Phe Met Leu Thr Leu Leu Gly Gly Phe Val Ala Asp Thr Phe                  |      |
|          85              90              95                                      |      |
| ctt gga cga tat ctt aca att ggc atc ttt acc act att caa gcc atg                  | 336  |
| Leu Gly Arg Tyr Leu Thr Ile Gly Ile Phe Thr Thr Ile Gln Ala Met                  |      |
|              100             105             110                                 |      |
| ggt gtt acc ata ttg acc atc tcc aca ata atc cca agc cta cga cca                  | 384  |
| Gly Val Thr Ile Leu Thr Ile Ser Thr Ile Ile Pro Ser Leu Arg Pro                  |      |
|          115             120             125                                     |      |
| cca aag tgt tcc cca ggg agc tca aca tgc att cca gca agt tcc aaa                  | 432  |
| Pro Lys Cys Ser Pro Gly Ser Ser Thr Cys Ile Pro Ala Ser Ser Lys                  |      |
| 130             135             140                                              |      |
| caa ctc atg gtt cta tac ata gca cta tac atg acg gcg ctc ggc acc                  | 480  |
| Gln Leu Met Val Leu Tyr Ile Ala Leu Tyr Met Thr Ala Leu Gly Thr                  |      |
| 145             150             155             160                              |      |
| ggc ggc ctg aaa tcc agc gtc tcc ggc ttc ggt tca gac cag ttc gac                  | 528  |
| Gly Gly Leu Lys Ser Ser Val Ser Gly Phe Gly Ser Asp Gln Phe Asp                  |      |
|              165             170             175                                 |      |
| gaa acc gac aag aaa gaa aga gga cag atg ata aaa ttc ttc aac tgg                  | 576  |
| Glu Thr Asp Lys Lys Glu Arg Gly Gln Met Ile Lys Phe Phe Asn Trp                  |      |
|          180             185             190                                     |      |
| ttc ttt ttc ttc att aat gtg gga tca ctt ggt gca gtg aca gta cta                  | 624  |
| Phe Phe Phe Phe Ile Asn Val Gly Ser Leu Gly Ala Val Thr Val Leu                  |      |
|          195             200             205                                     |      |
| gtg tat att caa gat aat ttg gga aga gaa tat ggt tat gga ata tgt                  | 672  |
| Val Tyr Ile Gln Asp Asn Leu Gly Arg Glu Tyr Gly Tyr Gly Ile Cys                  |      |
|      210             215             220                                         |      |
| gct tgt gct att gtt att ggt ttg gtc ata ttc tta tcg ggc aca aga                  | 720  |
| Ala Cys Ala Ile Val Ile Gly Leu Val Ile Phe Leu Ser Gly Thr Arg                  |      |
| 225             230             235             240                              |      |
| aaa tat cgt ttc aag aaa ctt gtg gga agt cca ttg aca caa att gct                  | 768  |
| Lys Tyr Arg Phe Lys Lys Leu Val Gly Ser Pro Leu Thr Gln Ile Ala                  |      |
|              245             250             255                                 |      |
| tca gtt ttt gtg gct gct tgg aac aaa agg cat atg gaa ttg cct tct                  | 816  |
| Ser Val Phe Val Ala Ala Trp Asn Lys Arg His Met Glu Leu Pro Ser                  |      |
|          260             265             270                                     |      |
| gat tct tct ctt tta tac aat att gat gat att cct ggg gat gga aac                  | 864  |
| Asp Ser Ser Leu Leu Tyr Asn Ile Asp Asp Ile Pro Gly Asp Gly Asn                  |      |
|      275             280             285                                         |      |
| aaa aaa gct aag cag agg ttg cct cac agc aag gaa ttc cgt ttc ttg                  | 912  |
| Lys Lys Ala Lys Gln Arg Leu Pro His Ser Lys Glu Phe Arg Phe Leu                  |      |
|  290             295             300                                             |      |
| gac aag gca gcc att aaa gta cag gac cct gaa tcc gct gga att acc                  | 960  |
| Asp Lys Ala Ala Ile Lys Val Gln Asp Pro Glu Ser Ala Gly Ile Thr                  |      |
| 305             310             315             320                              |      |
| gtg gta aat aaa tgg aac tta tca act tta acc gac gtt gaa gaa gta                  | 1008 |
| Val Val Asn Lys Trp Asn Leu Ser Thr Leu Thr Asp Val Glu Glu Val                  |      |
|              325             330             335                                 |      |

-continued

| | | |
|---|---|---|
| aaa ttg gta gtc cga atg tta cca aca tgg gcc acg acc att atg ttt<br>Lys Leu Val Val Arg Met Leu Pro Thr Trp Ala Thr Thr Ile Met Phe<br>340                     345                     350 | | 1056 |
| tgg act gtc tat gct caa atg aca aca ttt tcc gtg tca caa gct aca<br>Trp Thr Val Tyr Ala Gln Met Thr Thr Phe Ser Val Ser Gln Ala Thr<br>       355                     360                     365 | | 1104 |
| acc atg gac cgt cac atc gga aat ttc gaa att cct ccg gct tca ttg<br>Thr Met Asp Arg His Ile Gly Asn Phe Glu Ile Pro Pro Ala Ser Leu<br>370                     375                     380 | | 1152 |
| aca ctc ttc ttc gtc gga agt atc ctc cta acg tgc ata ttc tac gac<br>Thr Leu Phe Phe Val Gly Ser Ile Leu Leu Thr Cys Ile Phe Tyr Asp<br>385                     390                     395                     400 | | 1200 |
| cgc gct gtc gtt ccg gtt tgc cga cgt gtc ctc aac aac cct cac ggt<br>Arg Ala Val Val Pro Val Cys Arg Arg Val Leu Asn Asn Pro His Gly<br>                 405                     410                     415 | | 1248 |
| aca agc ccg ttg caa cgt att gca gtt ggc tta atc ctt tca att ata<br>Thr Ser Pro Leu Gln Arg Ile Ala Val Gly Leu Ile Leu Ser Ile Ile<br>             420                     425                     430 | | 1296 |
| gcc atg att gct gct gct tta act gaa gtg aaa aga ttg aat gtt gca<br>Ala Met Ile Ala Ala Ala Leu Thr Glu Val Lys Arg Leu Asn Val Ala<br>         435                     440                     445 | | 1344 |
| cat ttg cat gga ttg acc aat gat gct aat gca aag gtt cct ttg agt<br>His Leu His Gly Leu Thr Asn Asp Ala Asn Ala Lys Val Pro Leu Ser<br>450                     455                     460 | | 1392 |
| gtt ttt tgg tta gtc cca caa ttc ttg cta gta ggg gca ggt gag gca<br>Val Phe Trp Leu Val Pro Gln Phe Leu Leu Val Gly Ala Gly Glu Ala<br>465                     470                     475                     480 | | 1440 |
| ttt act tac att gga caa ctt gat ttc ttt cta agg gaa tgt cct aaa<br>Phe Thr Tyr Ile Gly Gln Leu Asp Phe Phe Leu Arg Glu Cys Pro Lys<br>                 485                     490                     495 | | 1488 |
| ggg atg aag aca atg agc aca ggg tta ttc ttg agt aca ctt tca cta<br>Gly Met Lys Thr Met Ser Thr Gly Leu Phe Leu Ser Thr Leu Ser Leu<br>             500                     505                     510 | | 1536 |
| ggg ttt ttc ttt agt tct att ttg gtg act ata gtg cac aag gtg aca<br>Gly Phe Phe Phe Ser Ser Ile Leu Val Thr Ile Val His Lys Val Thr<br>         515                     520                     525 | | 1584 |
| ggg aaa aac cca tgg tta gct gat aat tta aac caa ggg agg ctc tat<br>Gly Lys Asn Pro Trp Leu Ala Asp Asn Leu Asn Gln Gly Arg Leu Tyr<br>530                     535                     540 | | 1632 |
| gat ttc tat tgg cta ttg gca acg ttg agt gtg ttg aat ttg atg att<br>Asp Phe Tyr Trp Leu Leu Ala Thr Leu Ser Val Leu Asn Leu Met Ile<br>545                     550                     555                     560 | | 1680 |
| ttc ttg ttt att tcg aga cgg tat gtg tac aag gag aag agg ctt gct<br>Phe Leu Phe Ile Ser Arg Arg Tyr Val Tyr Lys Glu Lys Arg Leu Ala<br>                 565                     570                     575 | | 1728 |
| gag tgt ggg att gaa atg gag gat tca gaa cca gct tgc cac taa<br>Glu Cys Gly Ile Glu Met Glu Asp Ser Glu Pro Ala Cys His<br>             580                     585                     590 | | 1773 |

<210> SEQ ID NO 16
<211> LENGTH: 590
<212> TYPE: PRT
<213> ORGANISM: Nicotiana tabacum

<400> SEQUENCE: 16

Met Ala Leu Pro Glu Thr Gln Gln Asp Thr Lys Thr Leu Pro Asp Ala
1               5                   10                  15

Trp Asp Tyr Lys Gly Arg Pro Ala Val Arg Ser Ser Gly Gly Trp
            20                  25                  30

Ser Ser Ala Ala Met Ile Leu Gly Ile Glu Ala Val Glu Arg Leu Thr

-continued

```
            35                  40                  45
Thr Leu Gly Ile Ala Val Asn Leu Val Thr Tyr Leu Thr Gly Thr Met
    50                  55                  60
His Leu Gly Asn Ala Ser Ser Ala Asn Asn Val Thr Asn Phe Leu Gly
65                  70                  75                  80
Thr Ser Phe Met Leu Thr Leu Leu Gly Gly Phe Val Ala Asp Thr Phe
                85                  90                  95
Leu Gly Arg Tyr Leu Thr Ile Gly Ile Phe Thr Thr Ile Gln Ala Met
                100                 105                 110
Gly Val Thr Ile Leu Thr Ile Ser Thr Ile Ile Pro Ser Leu Arg Pro
            115                 120                 125
Pro Lys Cys Ser Pro Gly Ser Ser Thr Cys Ile Pro Ala Ser Ser Lys
        130                 135                 140
Gln Leu Met Val Leu Tyr Ile Ala Leu Tyr Met Thr Ala Leu Gly Thr
145                 150                 155                 160
Gly Gly Leu Lys Ser Ser Val Ser Gly Phe Gly Ser Asp Gln Phe Asp
                165                 170                 175
Glu Thr Asp Lys Lys Glu Arg Gly Gln Met Ile Lys Phe Phe Asn Trp
                180                 185                 190
Phe Phe Phe Phe Ile Asn Val Gly Ser Leu Gly Ala Val Thr Val Leu
                195                 200                 205
Val Tyr Ile Gln Asp Asn Leu Gly Arg Glu Tyr Gly Tyr Gly Ile Cys
            210                 215                 220
Ala Cys Ala Ile Val Ile Gly Leu Val Ile Phe Leu Ser Gly Thr Arg
225                 230                 235                 240
Lys Tyr Arg Phe Lys Lys Leu Val Gly Ser Pro Leu Thr Gln Ile Ala
                245                 250                 255
Ser Val Phe Val Ala Ala Trp Asn Lys Arg His Met Glu Leu Pro Ser
                260                 265                 270
Asp Ser Ser Leu Leu Tyr Asn Ile Asp Asp Ile Pro Gly Asp Gly Asn
                275                 280                 285
Lys Lys Ala Lys Gln Arg Leu Pro His Ser Lys Glu Phe Arg Phe Leu
        290                 295                 300
Asp Lys Ala Ala Ile Lys Val Gln Asp Pro Glu Ser Ala Gly Ile Thr
305                 310                 315                 320
Val Val Asn Lys Trp Asn Leu Ser Thr Leu Thr Asp Val Glu Glu Val
                325                 330                 335
Lys Leu Val Val Arg Met Leu Pro Thr Trp Ala Thr Thr Ile Met Phe
                340                 345                 350
Trp Thr Val Tyr Ala Gln Met Thr Thr Phe Ser Val Ser Gln Ala Thr
                355                 360                 365
Thr Met Asp Arg His Ile Gly Asn Phe Glu Ile Pro Pro Ala Ser Leu
        370                 375                 380
Thr Leu Phe Phe Val Gly Ser Ile Leu Leu Thr Cys Ile Phe Tyr Asp
385                 390                 395                 400
Arg Ala Val Val Pro Val Cys Arg Arg Val Leu Asn Asn Pro His Gly
                405                 410                 415
Thr Ser Pro Leu Gln Arg Ile Ala Val Gly Leu Ile Leu Ser Ile Ile
                420                 425                 430
Ala Met Ile Ala Ala Leu Thr Glu Val Lys Arg Leu Asn Val Ala
            435                 440                 445
His Leu His Gly Leu Thr Asn Asp Ala Asn Ala Lys Val Pro Leu Ser
        450                 455                 460
```

```
Val Phe Trp Leu Val Pro Gln Phe Leu Val Gly Ala Gly Glu Ala
465                 470                 475                 480

Phe Thr Tyr Ile Gly Gln Leu Asp Phe Phe Leu Arg Glu Cys Pro Lys
                485                 490                 495

Gly Met Lys Thr Met Ser Thr Gly Leu Phe Leu Ser Thr Leu Ser Leu
            500                 505                 510

Gly Phe Phe Ser Ser Ile Leu Val Thr Ile Val His Lys Val Thr
            515                 520                 525

Gly Lys Asn Pro Trp Leu Ala Asp Asn Leu Asn Gln Gly Arg Leu Tyr
            530                 535                 540

Asp Phe Tyr Trp Leu Leu Ala Thr Leu Ser Val Leu Asn Leu Met Ile
545                 550                 555                 560

Phe Leu Phe Ile Ser Arg Arg Tyr Val Tyr Lys Glu Lys Arg Leu Ala
                565                 570                 575

Glu Cys Gly Ile Glu Met Glu Asp Ser Glu Pro Ala Cys His
            580                 585                 590

<210> SEQ ID NO 17
<211> LENGTH: 1785
<212> TYPE: DNA
<213> ORGANISM: Nicotiana tabacum
<220> FEATURE:
<221> NAME/KEY: CDS
<222> LOCATION: (1)..(1782)

<400> SEQUENCE: 17 atg gca ctt cct gag aca cag caa gat tca aaa gct tta cca gac gct    48
Met Ala Leu Pro Glu Thr Gln Gln Asp Ser Lys Ala Leu Pro Asp Ala
1               5                   10                  15 tgg gat tac aaa ggc aga cca gcc ctt aga tcc tcc tct ggt ggt tgg    96
Trp Asp Tyr Lys Gly Arg Pro Ala Leu Arg Ser Ser Ser Gly Gly Trp
            20                  25                  30 gct agt ggt gca atg att tta ggt gtt gaa gct gtg gag agg cta aca   144
Ala Ser Gly Ala Met Ile Leu Gly Val Glu Ala Val Glu Arg Leu Thr
        35                  40                  45 aca cta ggg att gct gta aac tta gtg aca tat ttg act gga act atg   192
Thr Leu Gly Ile Ala Val Asn Leu Val Thr Tyr Leu Thr Gly Thr Met
    50                  55                  60 cat tta ggg aat gct tct tca gcc aac aat gtt acc aat ttt ctt gga   240
His Leu Gly Asn Ala Ser Ser Ala Asn Asn Val Thr Asn Phe Leu Gly
65                  70                  75                  80 act tct ttc atg ctc act tta ctt ggt ggt ttt gtc gcc gac act ttc   288
Thr Ser Phe Met Leu Thr Leu Leu Gly Gly Phe Val Ala Asp Thr Phe
                85                  90                  95 ctc gga agg tat ctt aca att ggt atc ttt gcc act gtt caa gca atg   336
Leu Gly Arg Tyr Leu Thr Ile Gly Ile Phe Ala Thr Val Gln Ala Met
            100                 105                 110 ggt gtt aca atc ttg acc atc tca act ata atc cca agc cta cga cca   384
Gly Val Thr Ile Leu Thr Ile Ser Thr Ile Ile Pro Ser Leu Arg Pro
        115                 120                 125 cca aaa tgt gaa caa gtt ggt agc tca tgc atc ccc gca aat agc       432
Pro Lys Cys Glu Gln Val Gly Ser Ser Ser Cys Ile Pro Ala Asn Ser
    130                 135                 140 aaa caa ctc atg gtc cta tat att gcc cta tac atg acg gct ctc ggc   480
Lys Gln Leu Met Val Leu Tyr Ile Ala Leu Tyr Met Thr Ala Leu Gly
145                 150                 155                 160 acc ggc ggc cta aaa tcg agc gtc tcc ggc ttt ggc acc gac caa ttc   528
Thr Gly Gly Leu Lys Ser Ser Val Ser Gly Phe Gly Thr Asp Gln Phe
                165                 170                 175
```

-continued

| | | |
|---|---|---|
| gac gat tct gac aag aaa gaa aag ggt caa atg ata aaa ttc ttc gat<br>Asp Asp Ser Asp Lys Lys Glu Lys Gly Gln Met Ile Lys Phe Phe Asp<br>180 185 190 | | 576 |
| tgg ttc ttt ttc ttt att aat gtt ggc tcg ctc ggt gca gtt acg gta<br>Trp Phe Phe Phe Phe Ile Asn Val Gly Ser Leu Gly Ala Val Thr Val<br>195 200 205 | | 624 |
| ttg gtt tat att caa gat aat ttg gga aga gag tgg ggt tat gga ata<br>Leu Val Tyr Ile Gln Asp Asn Leu Gly Arg Glu Trp Gly Tyr Gly Ile<br>210 215 220 | | 672 |
| tgt gca tgt gct att gtt att gca ctt gtt gtg ttc tta ttt ggg aca<br>Cys Ala Cys Ala Ile Val Ile Ala Leu Val Val Phe Leu Phe Gly Thr<br>225 230 235 240 | | 720 |
| agg aaa tat agg ttc aag aaa ctt ggg ggg agt cca ttg aca caa att<br>Arg Lys Tyr Arg Phe Lys Lys Leu Gly Gly Ser Pro Leu Thr Gln Ile<br>245 250 255 | | 768 |
| gct tca gtt att gtg gct gct tgg aag aaa agg cat ttg gaa tta ccc<br>Ala Ser Val Ile Val Ala Ala Trp Lys Lys Arg His Leu Glu Leu Pro<br>260 265 270 | | 816 |
| tca gat tct tca ctt ctc ttt gaa att gat gat att ttt ggt gaa gga<br>Ser Asp Ser Ser Leu Leu Phe Glu Ile Asp Asp Ile Phe Gly Glu Gly<br>275 280 285 | | 864 |
| aat aaa aaa agc aaa caa aag ttg ccc cat agc aag gag tac cga ttc<br>Asn Lys Lys Ser Lys Gln Lys Leu Pro His Ser Lys Glu Tyr Arg Phe<br>290 295 300 | | 912 |
| ttg gac aag gca gcc att aag gaa gat gat gac ctt gaa tct aat ggc<br>Leu Asp Lys Ala Ala Ile Lys Glu Asp Asp Asp Leu Glu Ser Asn Gly<br>305 310 315 320 | | 960 |
| act aac gtt gta atc aac aag tgg aaa tta gca acc tta acc gat gtt<br>Thr Asn Val Val Ile Asn Lys Trp Lys Leu Ala Thr Leu Thr Asp Val<br>325 330 335 | | 1008 |
| gaa gaa gta aaa ata tta atc aga atg ttg cca act tgg gcc aca act<br>Glu Glu Val Lys Ile Leu Ile Arg Met Leu Pro Thr Trp Ala Thr Thr<br>340 345 350 | | 1056 |
| att atg ttc tgg act gtc tat gca caa atg acc aca ttt tct gtg tca<br>Ile Met Phe Trp Thr Val Tyr Ala Gln Met Thr Thr Phe Ser Val Ser<br>355 360 365 | | 1104 |
| caa gct aca aca atg gat cgt cac att gga acc ttt gaa att cca cct<br>Gln Ala Thr Thr Met Asp Arg His Ile Gly Thr Phe Glu Ile Pro Pro<br>370 375 380 | | 1152 |
| gct aca ctc acc gta ttt ttc gtc gga agt ata ctc ttg acc gta att<br>Ala Thr Leu Thr Val Phe Phe Val Gly Ser Ile Leu Leu Thr Val Ile<br>385 390 395 400 | | 1200 |
| ttc tac gat agg att atc gtt ccg att tgt cgt cgt ttc atg aat aaa<br>Phe Tyr Asp Arg Ile Ile Val Pro Ile Cys Arg Arg Phe Met Asn Lys<br>405 410 415 | | 1248 |
| cct cat gga ctt acc cca tta caa aga att ttc aca ggc cta gtt ctt<br>Pro His Gly Leu Thr Pro Leu Gln Arg Ile Phe Thr Gly Leu Val Leu<br>420 425 430 | | 1296 |
| tca att ttg gcc atg att gct gct gcc cta aca gag gtt aag agg cta<br>Ser Ile Leu Ala Met Ile Ala Ala Ala Leu Thr Glu Val Lys Arg Leu<br>435 440 445 | | 1344 |
| aaa gtt gca cat ttg cat gga ttg acc aat gat gca aat gcc acg att<br>Lys Val Ala His Leu His Gly Leu Thr Asn Asp Ala Asn Ala Thr Ile<br>450 455 460 | | 1392 |
| cca ttg act gta ttt tgg tta gtt ccg caa ttc ttg cta gtg ggc gca<br>Pro Leu Thr Val Phe Trp Leu Val Pro Gln Phe Leu Leu Val Gly Ala<br>465 470 475 480 | | 1440 |
| ggt gaa gca ttt aca tat att ggc caa ctt gat ttt ttc tta agg gaa<br>Gly Glu Ala Phe Thr Tyr Ile Gly Gln Leu Asp Phe Phe Leu Arg Glu | | 1488 |

-continued

```
                        485                 490                 495
tgt cca aaa ggg atg aag aca atg agt aca ggg cta ttt ttg agt aca    1536
Cys Pro Lys Gly Met Lys Thr Met Ser Thr Gly Leu Phe Leu Ser Thr
            500                 505                 510 ctt gca ctt gga ttt ttc ttt agt tca att ttg gtt aca att gtg cat    1584
Leu Ala Leu Gly Phe Phe Phe Ser Ser Ile Leu Val Thr Ile Val His
        515                 520                 525 gtt gtg act gga aca aca aat cca tgg cta gct gat aat ttg aac caa    1632
Val Val Thr Gly Thr Thr Asn Pro Trp Leu Ala Asp Asn Leu Asn Gln
    530                 535                 540 ggg agg tta tat gat ttc tat tgg ctt ttg gca ata ttg agt gtg ttt    1680
Gly Arg Leu Tyr Asp Phe Tyr Trp Leu Leu Ala Ile Leu Ser Val Phe
545                 550                 555                 560 aat ttg atg ttt ttc ttg tat tcc tca aga aaa tat gtg tac aag gaa    1728
Asn Leu Met Phe Phe Leu Tyr Ser Ser Arg Lys Tyr Val Tyr Lys Glu
            565                 570                 575 aag aga ctt gct gaa atg ggg att gaa ttg gaa gat gat gga ccg gtt    1776
Lys Arg Leu Ala Glu Met Gly Ile Glu Leu Glu Asp Asp Gly Pro Val
        580                 585                 590 tgt cat tga                                                        1785
Cys His
```

<210> SEQ ID NO 18
<211> LENGTH: 594
<212> TYPE: PRT
<213> ORGANISM: Nicotiana tabacum

<400> SEQUENCE: 18

```
Met Ala Leu Pro Glu Thr Gln Gln Asp Ser Lys Ala Leu Pro Asp Ala
1               5                   10                  15

Trp Asp Tyr Lys Gly Arg Pro Ala Leu Arg Ser Ser Gly Gly Trp
            20                  25                  30

Ala Ser Gly Ala Met Ile Leu Gly Val Glu Ala Val Glu Arg Leu Thr
        35                  40                  45

Thr Leu Gly Ile Ala Val Asn Leu Val Thr Tyr Leu Thr Gly Thr Met
    50                  55                  60

His Leu Gly Asn Ala Ser Ser Ala Asn Asn Val Thr Asn Phe Leu Gly
65                  70                  75                  80

Thr Ser Phe Met Leu Thr Leu Leu Gly Gly Phe Val Ala Asp Thr Phe
            85                  90                  95

Leu Gly Arg Tyr Leu Thr Ile Gly Ile Phe Ala Thr Val Gln Ala Met
        100                 105                 110

Gly Val Thr Ile Leu Thr Ile Ser Thr Ile Ile Pro Ser Leu Arg Pro
    115                 120                 125

Pro Lys Cys Glu Gln Val Gly Ser Ser Cys Ile Pro Ala Asn Ser
130                 135                 140

Lys Gln Leu Met Val Leu Tyr Ile Ala Leu Tyr Met Thr Ala Leu Gly
145                 150                 155                 160

Thr Gly Gly Leu Lys Ser Ser Val Ser Gly Phe Gly Thr Asp Gln Phe
            165                 170                 175

Asp Asp Ser Asp Lys Lys Glu Lys Gly Gln Met Ile Lys Phe Phe Asp
        180                 185                 190

Trp Phe Phe Phe Ile Asn Val Gly Ser Leu Gly Ala Val Thr Val
    195                 200                 205

Leu Val Tyr Ile Gln Asp Asn Leu Gly Arg Glu Trp Gly Tyr Gly Ile
    210                 215                 220
```

-continued

```
Cys Ala Cys Ala Ile Val Ile Ala Leu Val Val Phe Leu Phe Gly Thr
225                 230                 235                 240

Arg Lys Tyr Arg Phe Lys Lys Leu Gly Gly Ser Pro Leu Thr Gln Ile
            245                 250                 255

Ala Ser Val Ile Val Ala Ala Trp Lys Lys Arg His Leu Glu Leu Pro
        260                 265                 270

Ser Asp Ser Ser Leu Leu Phe Glu Ile Asp Asp Ile Phe Gly Glu Gly
    275                 280                 285

Asn Lys Lys Ser Lys Gln Lys Leu Pro His Ser Lys Glu Tyr Arg Phe
290                 295                 300

Leu Asp Lys Ala Ala Ile Lys Glu Asp Asp Leu Glu Ser Asn Gly
305                 310                 315                 320

Thr Asn Val Val Ile Asn Lys Trp Lys Leu Ala Thr Leu Thr Asp Val
                325                 330                 335

Glu Glu Val Lys Ile Leu Ile Arg Met Leu Pro Thr Trp Ala Thr Thr
            340                 345                 350

Ile Met Phe Trp Thr Val Tyr Ala Gln Met Thr Thr Phe Ser Val Ser
        355                 360                 365

Gln Ala Thr Thr Met Asp Arg His Ile Gly Thr Phe Glu Ile Pro Pro
    370                 375                 380

Ala Thr Leu Thr Val Phe Phe Val Gly Ser Ile Leu Leu Thr Val Ile
385                 390                 395                 400

Phe Tyr Asp Arg Ile Ile Val Pro Ile Cys Arg Arg Phe Met Asn Lys
                405                 410                 415

Pro His Gly Leu Thr Pro Leu Gln Arg Ile Phe Thr Gly Leu Val Leu
            420                 425                 430

Ser Ile Leu Ala Met Ile Ala Ala Leu Thr Glu Val Lys Arg Leu
        435                 440                 445

Lys Val Ala His Leu His Gly Leu Thr Asn Asp Ala Asn Ala Thr Ile
450                 455                 460

Pro Leu Thr Val Phe Trp Leu Val Pro Gln Phe Leu Leu Val Gly Ala
465                 470                 475                 480

Gly Glu Ala Phe Thr Tyr Ile Gly Gln Leu Asp Phe Phe Leu Arg Glu
                485                 490                 495

Cys Pro Lys Gly Met Lys Thr Met Ser Thr Gly Leu Phe Leu Ser Thr
            500                 505                 510

Leu Ala Leu Gly Phe Phe Ser Ser Ile Leu Val Thr Ile Val His
        515                 520                 525

Val Val Thr Gly Thr Thr Asn Pro Trp Leu Ala Asp Asn Leu Asn Gln
530                 535                 540

Gly Arg Leu Tyr Asp Phe Tyr Trp Leu Leu Ala Ile Leu Ser Val Phe
545                 550                 555                 560

Asn Leu Met Phe Phe Leu Tyr Ser Ser Arg Lys Tyr Val Tyr Lys Glu
                565                 570                 575

Lys Arg Leu Ala Glu Met Gly Ile Glu Leu Glu Asp Asp Gly Pro Val
            580                 585                 590

Cys His
```

<210> SEQ ID NO 19
<211> LENGTH: 1785
<212> TYPE: DNA
<213> ORGANISM: Nicotiana tabacum
<220> FEATURE:
<221> NAME/KEY: CDS
<222> LOCATION: (1)..(1782)

<400> SEQUENCE: 19

```
atg gca ctt cct gag aca cag caa gat tca aaa gct tta cca gat gct    48
Met Ala Leu Pro Glu Thr Gln Gln Asp Ser Lys Ala Leu Pro Asp Ala
 1               5                  10                  15 tgg gat tac aaa gga aga cca gct ctt aga tcc tcc tct ggt ggt tgg    96
Trp Asp Tyr Lys Gly Arg Pro Ala Leu Arg Ser Ser Ser Gly Gly Trp
             20                  25                  30 gct agt ggt gca atg att tta ggt gtt gaa gct gtg gag agg cta aca   144
Ala Ser Gly Ala Met Ile Leu Gly Val Glu Ala Val Glu Arg Leu Thr
         35                  40                  45 aca cta ggg att gct gta aat ttg gtg aca tat ttg act gga act atg   192
Thr Leu Gly Ile Ala Val Asn Leu Val Thr Tyr Leu Thr Gly Thr Met
     50                  55                  60 cat tta ggg aat gct act gca gcc aac aat gtt acc aat ttt ctt gga   240
His Leu Gly Asn Ala Thr Ala Ala Asn Asn Val Thr Asn Phe Leu Gly
 65                  70                  75                  80 act tct ttc atg ctc act tta ttt ggt ggt ttt gtt gct gac act ttt   288
Thr Ser Phe Met Leu Thr Leu Phe Gly Gly Phe Val Ala Asp Thr Phe
                 85                  90                  95 ctc gga agg tat ctt aca att ggt atc ttt gcc act gtt caa gca atg   336
Leu Gly Arg Tyr Leu Thr Ile Gly Ile Phe Ala Thr Val Gln Ala Met
            100                 105                 110 ggt gtt aca atc ttg acc att tcc acc ata atc cca agc cta cgg cca   384
Gly Val Thr Ile Leu Thr Ile Ser Thr Ile Ile Pro Ser Leu Arg Pro
        115                 120                 125 cca aaa tgc gaa caa gtt ggt agc tca tca tgc atc ccc gca aat agc   432
Pro Lys Cys Glu Gln Val Gly Ser Ser Ser Cys Ile Pro Ala Asn Ser
    130                 135                 140 aaa caa ctt atg gtc cta tac att gcc cta tac atg acg gcg ctc ggc   480
Lys Gln Leu Met Val Leu Tyr Ile Ala Leu Tyr Met Thr Ala Leu Gly
145                 150                 155                 160 acc ggc ggc cta aaa tcg agc gtc tcc ggc ttt ggc acc gac caa ttc   528
Thr Gly Gly Leu Lys Ser Ser Val Ser Gly Phe Gly Thr Asp Gln Phe
                165                 170                 175 gac gat gct gac aaa aaa gaa aaa ggt caa atg ata aaa ttc ttc gat   576
Asp Asp Ala Asp Lys Lys Glu Lys Gly Gln Met Ile Lys Phe Phe Asp
            180                 185                 190 tgg ttc ttt ttc ttt att aat gta ggc tcg ctc ggt gct gtt aca gta   624
Trp Phe Phe Phe Phe Ile Asn Val Gly Ser Leu Gly Ala Val Thr Val
        195                 200                 205 ttg gtg tat att caa gat aat ttg gga aga gaa tgg ggt tat gga ata   672
Leu Val Tyr Ile Gln Asp Asn Leu Gly Arg Glu Trp Gly Tyr Gly Ile
    210                 215                 220 tgt gca tgt gct att gta att gga ctt gtt gtg ttc tta tct ggg aca   720
Cys Ala Cys Ala Ile Val Ile Gly Leu Val Val Phe Leu Ser Gly Thr
225                 230                 235                 240 aga aaa tat agg ttc aag aaa ctt gtg ggg agt cca ttg aca caa att   768
Arg Lys Tyr Arg Phe Lys Lys Leu Val Gly Ser Pro Leu Thr Gln Ile
                245                 250                 255 gct tca gtt att gtg gct gct tgg aaa aaa aga cat ttg gaa tta ctt   816
Ala Ser Val Ile Val Ala Ala Trp Lys Lys Arg His Leu Glu Leu Leu
            260                 265                 270 tca gat tct tca ctt ctc ttt gaa att gat gat att ttt ggt gaa gga   864
Ser Asp Ser Ser Leu Leu Phe Glu Ile Asp Asp Ile Phe Gly Glu Gly
        275                 280                 285 aat aaa aaa aac aag caa aag ttg cct cat agc aag gaa tac cga ttc   912
Asn Lys Lys Asn Lys Gln Lys Leu Pro His Ser Lys Glu Tyr Arg Phe
    290                 295                 300
```

| | | | | | | | | | | | | | | | | |
|---|---|---|---|---|---|---|---|---|---|---|---|---|---|---|---|---|
|ttg|gac|aag|gca|gca|att|aag|gaa|gat|cat|gat|ctt|gaa|tct|aat|ggc|960|
|Leu|Asp|Lys|Ala|Ala|Ile|Lys|Glu|Asp|His|Asp|Leu|Glu|Ser|Asn|Gly| |
|305| | | | |310| | | | |315| | | | |320| |

| | | | | | | | | | | | | | | | | |
|---|---|---|---|---|---|---|---|---|---|---|---|---|---|---|---|---|
|act|aac|gtt|gta|atc|aac|aag|tgg|aaa|tta|gca|acc|tta|acc|gat|gtt|1008|
|Thr|Asn|Val|Val|Ile|Asn|Lys|Trp|Lys|Leu|Ala|Thr|Leu|Thr|Asp|Val| |
| | | | |325| | | | |330| | | | |335| | |

| | | | | | | | | | | | | | | | | |
|---|---|---|---|---|---|---|---|---|---|---|---|---|---|---|---|---|
|gaa|gaa|gta|aaa|tta|tta|atc|aga|atg|tta|cca|act|tgg|gcc|aca|act|1056|
|Glu|Glu|Val|Lys|Leu|Leu|Ile|Arg|Met|Leu|Pro|Thr|Trp|Ala|Thr|Thr| |
| | | |340| | | | |345| | | | |350| | | |

| | | | | | | | | | | | | | | | | |
|---|---|---|---|---|---|---|---|---|---|---|---|---|---|---|---|---|
|att|atg|ttc|tgg|act|gtc|tat|gca|caa|atg|acc|aca|ttt|tct|gtg|tca|1104|
|Ile|Met|Phe|Trp|Thr|Val|Tyr|Ala|Gln|Met|Thr|Thr|Phe|Ser|Val|Ser| |
| | |355| | | | |360| | | | |365| | | | |

| | | | | | | | | | | | | | | | | |
|---|---|---|---|---|---|---|---|---|---|---|---|---|---|---|---|---|
|caa|gct|aca|aca|atg|gat|cgt|cac|att|gga|acc|ttt|gaa|att|cca|ccg|1152|
|Gln|Ala|Thr|Thr|Met|Asp|Arg|His|Ile|Gly|Thr|Phe|Glu|Ile|Pro|Pro| |
| |370| | | | |375| | | | |380| | | | | |

| | | | | | | | | | | | | | | | | |
|---|---|---|---|---|---|---|---|---|---|---|---|---|---|---|---|---|
|gct|tca|ctc|aca|gta|ttt|ttc|gtc|gga|agt|ata|ctc|ttg|acc|gta|att|1200|
|Ala|Ser|Leu|Thr|Val|Phe|Phe|Val|Gly|Ser|Ile|Leu|Leu|Thr|Val|Ile| |
|385| | | | |390| | | | |395| | | | |400| |

| | | | | | | | | | | | | | | | | |
|---|---|---|---|---|---|---|---|---|---|---|---|---|---|---|---|---|
|ttc|tac|gat|agg|gtt|atc|gtt|ccc|att|tgt|cgt|cgt|ttc|atg|aat|aaa|1248|
|Phe|Tyr|Asp|Arg|Val|Ile|Val|Pro|Ile|Cys|Arg|Arg|Phe|Met|Asn|Lys| |
| | | |405| | | | |410| | | | |415| | | |

| | | | | | | | | | | | | | | | | |
|---|---|---|---|---|---|---|---|---|---|---|---|---|---|---|---|---|
|cct|cat|gga|ctt|acc|cca|tta|caa|aga|att|ttc|aca|ggg|cta|gtt|ctt|1296|
|Pro|His|Gly|Leu|Thr|Pro|Leu|Gln|Arg|Ile|Phe|Thr|Gly|Leu|Val|Leu| |
| | |420| | | | |425| | | | |430| | | | |

| | | | | | | | | | | | | | | | | |
|---|---|---|---|---|---|---|---|---|---|---|---|---|---|---|---|---|
|tca|att|ttg|gcc|atg|ata|gcc|gct|gcc|cta|acg|gag|gtt|aag|agg|cta|1344|
|Ser|Ile|Leu|Ala|Met|Ile|Ala|Ala|Ala|Leu|Thr|Glu|Val|Lys|Arg|Leu| |
| | |435| | | | |440| | | | |445| | | | |

| | | | | | | | | | | | | | | | | |
|---|---|---|---|---|---|---|---|---|---|---|---|---|---|---|---|---|
|aaa|gtg|gca|cat|ttg|cat|gga|ttg|acc|aat|gat|gca|aat|gct|aca|att|1392|
|Lys|Val|Ala|His|Leu|His|Gly|Leu|Thr|Asn|Asp|Ala|Asn|Ala|Thr|Ile| |
|450| | | | |455| | | | |460| | | | | | |

| | | | | | | | | | | | | | | | | |
|---|---|---|---|---|---|---|---|---|---|---|---|---|---|---|---|---|
|cct|ttg|agt|gta|ttt|tgg|cta|gtt|ccg|caa|ttc|ttg|cta|gtg|ggg|gca|1440|
|Pro|Leu|Ser|Val|Phe|Trp|Leu|Val|Pro|Gln|Phe|Leu|Leu|Val|Gly|Ala| |
|465| | | | |470| | | | |475| | | | |480| |

| | | | | | | | | | | | | | | | | |
|---|---|---|---|---|---|---|---|---|---|---|---|---|---|---|---|---|
|ggt|gaa|gca|ttt|aca|tat|att|ggc|caa|ctt|gat|ttt|ttc|tta|agg|gaa|1488|
|Gly|Glu|Ala|Phe|Thr|Tyr|Ile|Gly|Gln|Leu|Asp|Phe|Phe|Leu|Arg|Glu| |
| | | | |485| | | | |490| | | | |495| | |

| | | | | | | | | | | | | | | | | |
|---|---|---|---|---|---|---|---|---|---|---|---|---|---|---|---|---|
|tgt|cca|aaa|gga|atg|aag|aca|atg|agt|aca|ggg|ctg|ttt|ttg|agt|aca|1536|
|Cys|Pro|Lys|Gly|Met|Lys|Thr|Met|Ser|Thr|Gly|Leu|Phe|Leu|Ser|Thr| |
| | | |500| | | | |505| | | | |510| | | |

| | | | | | | | | | | | | | | | | |
|---|---|---|---|---|---|---|---|---|---|---|---|---|---|---|---|---|
|ctt|gca|ttg|ggg|ttt|ttc|ttt|agt|tca|att|ttg|gtt|aca|att|gtg|cat|1584|
|Leu|Ala|Leu|Gly|Phe|Phe|Phe|Ser|Ser|Ile|Leu|Val|Thr|Ile|Val|His| |
| | |515| | | | |520| | | | |525| | | | |

| | | | | | | | | | | | | | | | | |
|---|---|---|---|---|---|---|---|---|---|---|---|---|---|---|---|---|
|gtt|gtg|act|ggg|aca|aca|aat|cca|tgg|cta|gct|gat|aat|ttg|aac|caa|1632|
|Val|Val|Thr|Gly|Thr|Thr|Asn|Pro|Trp|Leu|Ala|Asp|Asn|Leu|Asn|Gln| |
|530| | | | |535| | | | |540| | | | | | |

| | | | | | | | | | | | | | | | | |
|---|---|---|---|---|---|---|---|---|---|---|---|---|---|---|---|---|
|ggg|agg|tta|tat|gat|ttc|tat|tgg|ctt|ttg|gct|ata|ttg|agt|gtg|ttg|1680|
|Gly|Arg|Leu|Tyr|Asp|Phe|Tyr|Trp|Leu|Leu|Ala|Ile|Leu|Ser|Val|Leu| |
|545| | | | |550| | | | |555| | | | |560| |

| | | | | | | | | | | | | | | | | |
|---|---|---|---|---|---|---|---|---|---|---|---|---|---|---|---|---|
|aat|ttg|atg|ttt|ttc|ttg|tac|ttt|tca|aga|aaa|tat|gtg|tac|aag|gag|1728|
|Asn|Leu|Met|Phe|Phe|Leu|Tyr|Phe|Ser|Arg|Lys|Tyr|Val|Tyr|Lys|Glu| |
| | | | |565| | | | |570| | | | |575| | |

| | | | | | | | | | | | | | | | | |
|---|---|---|---|---|---|---|---|---|---|---|---|---|---|---|---|---|
|aag|aga|ctt|gct|gaa|atg|ggg|att|gaa|ttg|gaa|gat|gat|gga|ccg|gtt|1776|
|Lys|Arg|Leu|Ala|Glu|Met|Gly|Ile|Glu|Leu|Glu|Asp|Asp|Gly|Pro|Val| |
| | | |580| | | | |585| | | | |590| | | |

| | |
|---|---|
|tgt cat tga|1785|
|Cys His| |

<210> SEQ ID NO 20
<211> LENGTH: 594
<212> TYPE: PRT

<213> ORGANISM: Nicotiana tabacum

<400> SEQUENCE: 20

```
Met Ala Leu Pro Glu Thr Gln Gln Asp Ser Lys Ala Leu Pro Asp Ala
1               5                   10                  15
Trp Asp Tyr Lys Gly Arg Pro Ala Leu Arg Ser Ser Gly Gly Trp
            20                  25                  30
Ala Ser Gly Ala Met Ile Leu Gly Val Glu Ala Val Glu Arg Leu Thr
        35                  40                  45
Thr Leu Gly Ile Ala Val Asn Leu Val Thr Tyr Leu Thr Gly Thr Met
    50                  55                  60
His Leu Gly Asn Ala Thr Ala Ala Asn Asn Val Thr Asn Phe Leu Gly
65                  70                  75                  80
Thr Ser Phe Met Leu Thr Leu Phe Gly Gly Phe Val Ala Asp Thr Phe
                85                  90                  95
Leu Gly Arg Tyr Leu Thr Ile Gly Ile Phe Ala Thr Val Gln Ala Met
            100                 105                 110
Gly Val Thr Ile Leu Thr Ile Ser Thr Ile Ile Pro Ser Leu Arg Pro
        115                 120                 125
Pro Lys Cys Glu Gln Val Gly Ser Ser Ser Cys Ile Pro Ala Asn Ser
    130                 135                 140
Lys Gln Leu Met Val Leu Tyr Ile Ala Leu Tyr Met Thr Ala Leu Gly
145                 150                 155                 160
Thr Gly Gly Leu Lys Ser Ser Val Ser Gly Phe Gly Thr Asp Gln Phe
                165                 170                 175
Asp Asp Ala Asp Lys Lys Glu Lys Gly Gln Met Ile Lys Phe Phe Asp
            180                 185                 190
Trp Phe Phe Phe Ile Asn Val Gly Ser Leu Gly Ala Val Thr Val
        195                 200                 205
Leu Val Tyr Ile Gln Asp Asn Leu Gly Arg Glu Trp Gly Tyr Gly Ile
    210                 215                 220
Cys Ala Cys Ala Ile Val Ile Gly Leu Val Val Phe Leu Ser Gly Thr
225                 230                 235                 240
Arg Lys Tyr Arg Phe Lys Lys Leu Val Gly Ser Pro Leu Thr Gln Ile
                245                 250                 255
Ala Ser Val Ile Val Ala Ala Trp Lys Lys Arg His Leu Glu Leu Leu
            260                 265                 270
Ser Asp Ser Ser Leu Leu Phe Glu Ile Asp Asp Ile Phe Gly Glu Gly
        275                 280                 285
Asn Lys Lys Asn Lys Gln Lys Leu Pro His Ser Lys Glu Tyr Arg Phe
    290                 295                 300
Leu Asp Lys Ala Ala Ile Lys Glu Asp His Asp Leu Glu Ser Asn Gly
305                 310                 315                 320
Thr Asn Val Val Ile Asn Lys Trp Lys Leu Ala Leu Thr Asp Val
                325                 330                 335
Glu Glu Val Lys Leu Leu Ile Arg Met Leu Pro Thr Trp Ala Thr Thr
            340                 345                 350
Ile Met Phe Trp Thr Val Tyr Ala Gln Met Thr Thr Phe Ser Val Ser
        355                 360                 365
Gln Ala Thr Thr Met Asp Arg His Ile Gly Thr Phe Glu Ile Pro Pro
    370                 375                 380
Ala Ser Leu Thr Val Phe Phe Val Gly Ser Ile Leu Leu Thr Val Ile
385                 390                 395                 400
```

```
Phe Tyr Asp Arg Val Ile Val Pro Ile Cys Arg Arg Phe Met Asn Lys
                405                 410                 415
Pro His Gly Leu Thr Pro Leu Gln Arg Ile Phe Thr Gly Leu Val Leu
            420                 425                 430
Ser Ile Leu Ala Met Ile Ala Ala Leu Thr Glu Val Lys Arg Leu
        435                 440                 445
Lys Val Ala His Leu His Gly Leu Thr Asn Asp Ala Asn Ala Thr Ile
450                 455                 460
Pro Leu Ser Val Phe Trp Leu Val Pro Gln Phe Leu Val Gly Ala
465                 470                 475                 480
Gly Glu Ala Phe Thr Tyr Ile Gly Gln Leu Asp Phe Phe Leu Arg Glu
                485                 490                 495
Cys Pro Lys Gly Met Lys Thr Met Ser Thr Gly Leu Phe Leu Ser Thr
            500                 505                 510
Leu Ala Leu Gly Phe Phe Ser Ser Ile Leu Val Thr Ile Val His
        515                 520                 525
Val Val Thr Gly Thr Thr Asn Pro Trp Leu Ala Asp Asn Leu Asn Gln
530                 535                 540
Gly Arg Leu Tyr Asp Phe Tyr Trp Leu Leu Ala Ile Leu Ser Val Leu
545                 550                 555                 560
Asn Leu Met Phe Phe Leu Tyr Phe Ser Arg Lys Tyr Val Tyr Lys Glu
                565                 570                 575
Lys Arg Leu Ala Glu Met Gly Ile Glu Leu Glu Asp Asp Gly Pro Val
            580                 585                 590
Cys His

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Sense
      primer N-1

<400> SEQUENCE: 21
atggcacttc ctgaaacaca acaa                                          24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Anti-sense
      primer N-2

<400> SEQUENCE: 22
ttagtggcaa gctggttctg aatc                                          24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Sense
      primer N-3

<400> SEQUENCE: 23
atggcacttc ctgagacaca gc                                            22

<210> SEQ ID NO 24
```

```
<211> LENGTH: 23
<212> TYPE: DNA
<213> ORGANISM: Artificial Sequence
<220> FEATURE:
<223> OTHER INFORMATION: Description of Artificial Sequence: Anti-sense
      primer N-4

<400> SEQUENCE: 24
tcaatgacaa accggtccat cat                                            23

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: 433-458
      forward primer

<400> SEQUENCE: 25
aaacaactta tggtcctata cattgc                                         26

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: 777-751
      reverse primer

<400> SEQUENCE: 26
aactgaagca atttgtgtca atggact                                        27

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Forward
      primer for nrt1.1 group

<400> SEQUENCE: 27
aacgttgagt gtgttgaatt tgat                                           24

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Reverse
      primer for nrt1.1 group

<400> SEQUENCE: 28
ctggttctga atcctccatt tc                                             22

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Forward
      primer for nrt1.2 group

<400> SEQUENCE: 29
tgttgtgact gggacaacaa atc                                            23

<210> SEQ ID NO 30
<211> LENGTH: 24
```

```
<212> TYPE: DNA
<213> ORGANISM: Artificial Sequence
<220> FEATURE:
<223> OTHER INFORMATION: Description of Artificial Sequence: Reverse
      primer for nrt1.2 group

<400> SEQUENCE: 30
aatccccatt tcagcaagtc tctt                                          24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Forward
      primer for ATP synthase

<400> SEQUENCE: 31
aaacgattgc tctgaaaggt catc                                          24

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Reverse
      primer for ATP synthase

<400> SEQUENCE: 32
gcccctggaa agtatgtcga c                                             21
```